(12) United States Patent
Boux et al.

(10) Patent No.: US 6,964,851 B2
(45) Date of Patent: Nov. 15, 2005

(54) COMPOSITIONS AND METHODS FOR DETECTING STRESS-INDUCIBLE PROTEINS

(75) Inventors: Heather A. Boux, Victoria (CA); Geraldine S. Wong, Victoria (CA); Henry Rodriguez, North Saanich (CA)

(73) Assignee: Stressgen Biotechnologies Corp., Victoria (CA)

( * ) Notice: Subject to any disclaimer, the term of this patent is extended or adjusted under 35 U.S.C. 154(b) by 429 days.

(21) Appl. No.: 09/733,179

(22) Filed: Dec. 7, 2000

(65) Prior Publication Data

US 2003/0073160 A1 Apr. 17, 2003

Related U.S. Application Data

(60) Provisional application No. 60/169,535, filed on Dec. 7, 1999.

(51) Int. Cl.$^7$ ............................................. G01N 33/53
(52) U.S. Cl. ...................... 435/7.1; 435/7.92; 435/69.1; 435/320.1; 436/86; 436/547
(58) Field of Search ................................ 435/7.1, 7.92, 435/69.1, 320.1; 436/86, 547

(56) References Cited

U.S. PATENT DOCUMENTS

| | | | |
|---|---|---|---|
| 5,493,008 A | | 2/1996 | Fox et al. |
| 5,929,220 A | | 7/1999 | Tong et al. |
| 6,268,548 B1 | * | 7/2001 | Elthon et al. ............... 800/289 |
| 6,451,316 B1 | * | 9/2002 | Srivastava ............... 424/193.1 |
| 2003/0064072 A9 | * | 4/2003 | Rosen et al. ............. 424/184.1 |

FOREIGN PATENT DOCUMENTS

| | | |
|---|---|---|
| WO | WO 97/28688 | 8/1997 |
| WO | WO 99/54464 | 10/1999 |

OTHER PUBLICATIONS

Campbell (Monoclonal Antibody Technology Campbell eds, 1986).*
Schild et al. Curr. Opinion in Immu. 1999 11: 109.*
Birkelund et al., "Characterization of a Linear Epitope on *Chlamydia trachomatis* Serovar L2 DnaK–Like Protein" *Infection and Immunity* 62:2051–2057, 1994.
Botzler et al., "Definition of extracellular localized epitopes of Hsp70 involved in an NK immune response" *Cell Stress & Chaperones* 3:6–11, 1998.
Parsian et al., "The human Hsp70B gene at the *HSPA7* locus of chromosome 1 is transcribed but non–functional" *Biochemica et Biophysica Acta* 1494:201–205, 2000.
Dezeure et al. *Biochimica et Biophysica Acta 1174:*17–26, 1993.
Schiller et al. *J. Mol. Biol. 203:*97–105, 1988.
Bachelet et al., *Cell Stress & Chaperones 3:*168–176, 1998.
Bratton et al., *Int. J. Hyperthermia 13:*157–168, 1997.
Chang et al., *Proc. Nat. Acad. Sci. USA 93:*136–140, 1996.
Greene et al., *Mol. Cell Biol. 7:*3646–55, 1987.
Hansen et al., *Exp. Cell Research 192:*587–596, 1991.
Kelly et al., *J. Appl. Physiol. 81:*2379–2385, 1996.
Kohler et al., *Euro. J. Immunol. 6:*511–519, 1976.
Leung et al., *Biochem. J. 267:*125–132, 1990.
Leung et al., *Genomics 12:*74–79, 1992.
Mangurten et al., *Cell Stress & Chaperones 2:*168–174, 1997.
Minowada et al., *J. Clin. Invest. 95:*3–12, 1995.
Oberringer et al., *Biochemical and Biophysical Research Communications 214:*1009–1014, 1995.
Pockley et al., *Immunol. Invest. 27:*367–77, 1998.
Suzuki et al., *Radiation Research 149:*195–201, 1998.
Tavaria et al., *Cell Stress & Chaperones 1:*23–28, 1996.
Turman et al., *Biochemical and Molecular Medicine 60:*49–58, 1997.
Wu et al., *Proc. Natl. Acad. Sci., USA 83:*629–633, 1986.

* cited by examiner

*Primary Examiner*—Long V. Le
*Assistant Examiner*—Jacob Cheu
(74) *Attorney, Agent, or Firm*—Fish & Richardson P.C.

(57) ABSTRACT

Compositions and methods for detection of the stress-inducible Hsp70B' protein are disclosed. These include antibodies directed against particular amino acid regions of Hsp70B' and various peptides corresponding, or antigenically equivalent, to the regions. The ability to generate anti-Hsp70B' antibodies to defined epitopes permits a variety of in vitro and in vivo uses.

21 Claims, 3 Drawing Sheets

```
  1 mqaprelavg idlgttyscv gvfqqgrvei landqgnrtt psyvaftdte rlvgdaaksq
 61 aalnphntvf dakrligrkf adttvqsdmk hwpfrvvseg gkpkvpvsyr gedktfypee
121 issmvlskmk etaeaylgqp vkhavitvpa yfndsqrqat kdagaiagin vlriinepta
181 aaiaygldrr gagernvlif dlgggtfdvs vlsidagvfe vkatagdthl ggedfdnrlv
241 nhfmeefrrk hgkdlsgnkr algrlrtace rakrtlssst qatleidslf egvdfytsit
301 rarfeelcsd lfrstlepve kalrdakldk aqihdvvlvg gstripkvqk llqdlfngke
361 lnksinpdea vaygaavqaa vlmgdkcekv qdllldvap lslgletagg vmttliqrna
421 tiptkqtqtf ttysdnqpgv fiqvyegera mtkdnnllgr felsgippap rgvpqievtf
481 didangilsv tatdrstgka nkititndkg rlskeeverm vheaeqykae deaqrdrvaa
541 knsleahvfh vkgslqeesl rdkipeedrr kmqdkcrevl awlehnqlae keeyehqkre
601 leqicrpifs rlyggpgvpg gsscgtqarq gdpstgpiie evd
```

FIG. 2

SEQUENCE LISTING

<160> NUMBER OF SEQ ID NOS: 15

<210> SEQ ID NO 1
<211> LENGTH: 21
<212> TYPE: PRT
<213> ORGANISM: Homo sapiens

<400> SEQUENCE: 1

Val Pro Gly Gly Ser Ser Cys Gly Thr Gln Ala Arg Gln Gly Asp Pro
 1               5                  10                  15

Ser Thr Gly Pro Ile
            20

<210> SEQ ID NO 2
<211> LENGTH: 15
<212> TYPE: PRT
<213> ORGANISM: Homo sapiens

<400> SEQUENCE: 2

Cys Gly Thr Gln Ala Arg Gln Gly Asp Pro Ser Thr Gly Pro Ile
 1               5                  10                  15

<210> SEQ ID NO 3
<211> LENGTH: 12
<212> TYPE: PRT
<213> ORGANISM: Homo sapiens

<400> SEQUENCE: 3

Cys Gly Thr Gln Ala Arg Gln Gly Asp Pro Ser Thr
1               5                   10

<210> SEQ ID NO 4
<211> LENGTH: 16
<212> TYPE: PRT
<213> ORGANISM: Homo sapiens

<400> SEQUENCE: 4

Arg Asp Lys Ile Pro Glu Glu Asp Arg Arg Lys Met Gln Asp Lys Cys
1               5                   10                  15

<210> SEQ ID NO 5
<211> LENGTH: 13
<212> TYPE: PRT
<213> ORGANISM: Homo sapiens

<400> SEQUENCE: 5

Arg Asp Lys Ile Pro Glu Glu Asp Arg Arg Lys Met Gln
1               5                   10

<210> SEQ ID NO 6
<211> LENGTH: 28
<212> TYPE: PRT
<213> ORGANISM: Homo sapiens

<400> SEQUENCE: 6

Ala His Val Phe His Val Lys Gly Ser Leu Gln Glu Glu Ser Leu Arg
1               5                   10                  15

Asp Lys Ile Pro Glu Glu Asp Arg Arg Lys Met Gln
            20                  25

<210> SEQ ID NO 7
<211> LENGTH: 14
<212> TYPE: PRT
<213> ORGANISM: Homo sapiens

<400> SEQUENCE: 7

Ala His Val Phe His Val Lys Gly Ser Leu Gln Glu Glu Ser
1               5                   10

<210> SEQ ID NO 8
<211> LENGTH: 11
<212> TYPE: PRT
<213> ORGANISM: Homo sapiens

<400> SEQUENCE: 8

Met Ala Pro Arg Glu Leu Ala Val Gly Ile Asp
1               5                   10

<210> SEQ ID NO 9
<211> LENGTH: 13
<212> TYPE: PRT
<213> ORGANISM: Homo sapiens

<400> SEQUENCE: 9

Met Gln Ala Pro Arg Glu Leu Ala Val Gly Ile Asp Cys

-continued

```
         1               5                  10
```

<210> SEQ ID NO 10
<211> LENGTH: 15
<212> TYPE: PRT
<213> ORGANISM: Homo sapiens

<400> SEQUENCE: 10

```
Gly Ser Leu Gln Glu Glu Ser Leu Arg Asp Lys Ile Pro Glu Glu
 1               5                  10                  15
```

<210> SEQ ID NO 11
<211> LENGTH: 643
<212> TYPE: PRT
<213> ORGANISM: Homo sapiens

<400> SEQUENCE: 11

```
Met Gln Ala Pro Arg Glu Leu Ala Val Gln Ile Asp Leu Gln Thr Thr
 1               5                  10                  15

Tyr Ser Cys Val Gly Val Phe Gln Gln Gly Arg Val Glu Ile Leu Ala
                20                  25                  30

Asn Asp Gln Gly Asn Arg Thr Thr Pro Ser Tyr Val Ala Phe Thr Asp
            35                  40                  45

Thr Glu Arg Leu Val Gln Asp Ala Ala Lys Ser Gln Ala Ala Leu Asn
        50                  55                  60

Pro His Asn Thr Val Phe Asp Ala Lys Arg Leu Ile Gly Arg Lys Phe
    65                  70                  75                  80

Ala Asp Thr Thr Val Gln Ser Asp Met Lys His Trp Pro Phe Arg Val
                85                  90                  95

Val Ser Glu Gly Gly Lys Pro Lys Val Pro Val Ser Tyr Arg Gly Glu
            100                 105                 110

Asp Lys Thr Phe Tyr Pro Glu Glu Ile Ser Ser Met Val Leu Ser Lys
        115                 120                 125

Met Lys Glu Thr Ala Glu Ala Tyr Leu Gly Gln Pro Val Lys His Ala
    130                 135                 140

Val Ile Thr Val Pro Ala Tyr Phe Asn Asp Ser Gln Arg Gln Ala Thr
145                 150                 155                 160

Lys Asp Ala Gly Ala Ile Ala Gly Leu Asn Val Leu Arg Ile Ile Asn
                165                 170                 175

Glu Pro Thr Ala Ala Ala Ile Ala Tyr Gly Leu Asp Arg Arg Gly Ala
            180                 185                 190

Gly Glu Arg Asn Val Leu Ile Phe Asp Leu Gly Gly Gly Thr Phe Asp
        195                 200                 205

Val Ser Val Leu Ser Ile Asp Ala Gly Val Phe Glu Val Lys Ala Thr
    210                 215                 220

Ala Gly Asp Thr His Leu Gly Gly Glu Asp Phe Asp Asn Arg Leu Val
225                 230                 235                 240

Asn His Phe Met Glu Glu Phe Arg Arg Lys His Gly Lys Asp Leu Ser
                245                 250                 255

Gly Asn Lys Arg Ala Leu Gly Arg Leu Arg Thr Ala Cys Glu Arg Ala
            260                 265                 270

Lys Arg Thr Leu Ser Ser Thr Gln Ala Thr Leu Glu Ile Asp Ser
        275                 280                 285

Leu Phe Glu Gly Val Asp Phe Tyr Thr Ser Ile Thr Arg Ala Arg Phe
    290                 295                 300

Glu Glu Leu Cys Ser Asp Leu Phe Arg Ser Thr Leu Glu Pro Val Glu
```

```
                305                 310                 315                 320
Lys Ala Leu Arg Asp Ala Lys Leu Asp Lys Ala Gln Ile His Asp Val
                325                 330                 335
Val Leu Val Gly Gly Ser Thr Arg Ile Pro Lys Val Gln Lys Leu Leu
                340                 345                 350
Gln Asp Phe Phe Asn Gly Lys Glu Leu Asn Lys Ser Ile Asn Pro Asp
                355                 360                 365
Glu Ala Val Ala Tyr Gly Ala Ala Val Gln Ala Ala Val Leu Met Gly
                370                 375                 380
Asp Lys Cys Glu Lys Val Gln Asp Leu Leu Leu Leu Asp Val Ala Pro
385                 390                 395                 400
Leu Ser Leu Gly Leu Glu Thr Ala Gly Gly Val Met Thr Thr Leu Ile
                405                 410                 415
Gln Arg Asn Ala Thr Ile Pro Thr Lys Gln Thr Gln Thr Phe Thr Thr
                420                 425                 430
Tyr Ser Asp Asn Gln Pro Gly Val Phe Ile Gln Val Tyr Glu Gly Glu
                435                 440                 445
Arg Ala Met Thr Lys Asp Asn Asn Leu Leu Gly Arg Phe Glu Leu Ser
                450                 455                 460
Gly Ile Pro Pro Ala Pro Arg Gly Val Pro Gln Ile Glu Val Thr Phe
465                 470                 475                 480
Asp Ile Asp Ala Asn Gly Ile Leu Ser Val Thr Ala Thr Asp Arg Ser
                485                 490                 495
Thr Gly Lys Ala Asn Lys Ile Thr Ile Thr Asn Asp Lys Gly Arg Leu
                500                 505                 510
Ser Lys Glu Glu Val Glu Arg Met Val His Glu Ala Glu Gln Tyr Lys
                515                 520                 525
Ala Glu Asp Glu Ala Gln Arg Asp Arg Val Ala Ala Lys Asn Ser Leu
                530                 535                 540
Glu Ala His Val Phe His Val Lys Gly Ser Leu Gln Glu Glu Ser Leu
545                 550                 555                 560
Arg Asp Lys Ile Pro Glu Glu Asp Arg Arg Lys Met Gln Asp Lys Cys
                565                 570                 575
Arg Glu Val Leu Ala Trp Leu Glu His Asn Gln Leu Ala Glu Lys Glu
                580                 585                 590
Glu Tyr Glu His Gln Lys Arg Glu Leu Glu Gln Ile Cys Arg Pro Ile
                595                 600                 605
Phe Ser Arg Leu Tyr Gly Gly Pro Gly Val Pro Gly Gly Ser Ser Cys
                610                 615                 620
Gly Thr Gln Ala Arg Gln Gly Asp Pro Ser Thr Gly Pro Ile Ile Glu
625                 630                 635                 640
Glu Val Asp

<210> SEQ ID NO 12
<211> LENGTH: 34
<212> TYPE: DNA
<213> ORGANISM: Homo sapiens

<400> SEQUENCE: 12
gaagcttcac atatgcaggc cccacgggag ctcg                                    34

<210> SEQ ID NO 13
<211> LENGTH: 30
<212> TYPE: DNA
<213> ORGANISM: Homo sapiens
```

```
<400> SEQUENCE: 13
gaagctcgag tcaatcaacc tcctcaatga                                    30

<210> SEQ ID NO 14
<211> LENGTH: 31
<212> TYPE: DNA
<213> ORGANISM: Homo sapiens

<400> SEQUENCE: 14
tgacaagctt agaattcttc catgaagtgg t                                  31

<210> SEQ ID NO 15
<211> LENGTH: 14
<212> TYPE: PRT
<213> ORGANISM: Homo sapiens

<400> SEQUENCE: 15

Cys Arg Asp Lys Ile Pro Glu Glu Asp Arg Arg Lys Met Gln
 1               5                  10
```

COMPOSITIONS AND METHODS FOR DETECTING STRESS-INDUCIBLE PROTEINS

The present application claims the benefit of U.S. Ser. No. 60/169,535 filed Dec. 7, 1999.

The present invention features compositions and methods for detecting the stress-inducible protein Hsp70B'. More specifically, the invention features antibodies that specifically bind Hsp70B' or fragments, antigenically equivalent portions, or epitopes thereof.

BACKGROUND OF THE INVENTION

Cells within most organisms have evolved a mechanism known as the "cellular stress response" to cope with adverse changes in their environment. The response is a universal cellular defense mechanism that results in increased expression of a class of proteins referred to as "heat shock" or "stress" proteins. The conditions that trigger the response include: a rise in temperature, hypoxia, irradiation, nutritional deficiencies, acute exercise, infection, or exposure to a metabolic insult such as a proinflammatory cytokine, a heavy metal, an amino acid analogue, or a metabolic poison (Kelly et al., *J. Appl. Physiol.* 81:2379–2385, 1996; Minowada and Welch, *J. Clin. Invest.* 95:3–12, 1995).

Stress proteins are also essential for normal cellular function and many are constitutively expressed. They are believed to help regulate the cell cycle and cellular differentiation and to maintain the cell at critical stages of organ development (Birnbaum, *Springer Semin. Immunopathol.* 17:107–118, 1995). Some stress proteins are molecular chaperones that facilitate the correct folding or conformation of nascent polypeptides, direct intracellular trafficking of proteins, protect proteins against denaturation, and assist in the renaturation of unfolded proteins (Macario, *Int. J. Clin. Lab Res.* 25:59–70, 1995). Stress proteins also participate in antigen presentation and nuclear receptor binding and act as anti-apoptotic agents.

The HSP70 family of stress proteins includes at least 11 different genes that encode highly related protein isoforms ranging in size from 66 kDa to 110 kDa (Tavaria et al., *Cell Stress & Chaperones* 1:23–28, 1996). Members of this family help regulate protein synthesis and translocation, protein-protein interactions, thermotolerance, and protein degradation (Mangurten et al., *Cell Stress & Chaperones* 2:168–174, 1997).

Members of the human hsp70 gene family also display considerable structural and sequence similarity; the greatest sequence divergence is in the untranslated regions and extreme C-terminal coding regions (Leung et al., *Genomics* 12:74–79, 1992). Individual Hsp70 family members differ in their levels of basal expression and are induced under different conditions (Leung et al., *Genomics* 12:74–79, 1992). The majority of Hsp70 protein isoforms are synthesized constitutively, but their expression may be up-regulated following exposure to an environmental insult. These proteins bind ATP through an ATP-binding cassette at their N-terminus and have a large C-terminus peptide-binding domain (Maio et al., *Guidebook to Molecular Chaperones and Protein-Folding Catalysts*, Sambrook & Tooze Publication, Oxford University Press, 1997). This peptide binding function allows Hsp70 proteins to play a significant role in the protection and folding of nascent proteins after synthesis, in the translocation of proteins through membranes, and in the protection and repair of stress-induced protein damage (Minowada and Welch, *J. Clin. Invest.* 95:3–12, 1995).

Members of the human HSP70 protein family associate with distinct cellular compartments. Prominent family members include: i) the constitutive Hsc70 (or cognate) protein, which is present within the cytosol and nucleus, ii) the highly stress-inducible Hsp70A protein, which is present within the cytosol, nucleus, and nucleolus (this protein is present at basal levels in unstressed human cells), iii) the strictly stress-inducible Hsp70B' protein and its closely related isoform Hsp70B, iv) the constitutive glucose regulated 78 kDa protein (or BiP), which is present within the lumen of the endoplasmic reticulum, and v) the glucose regulated 75 kDa protein (Grp75 or mtHsp 75), which is present within mitochondria (Tavaria et al., *Cell Stress & Chaperones* 1:23–28, 1996).

Antibodies have been raised against Hsp70 family members that are expressed at basal levels and whose expression can be induced to high levels (i.e., Grp75, and Hsp70A) and to the constitutive Hsp70 family members (e.g., Hsc70, BiP). However, there are no antibodies that specifically bind the strictly inducible Hsp70B' protein or its homologue, Hsp70B. Thus, immunological based assays (such as immunoblotting, EIA, and immunohistochemistry)) have been practiced with antibodies that are not strictly stress inducible. The results obtained with these assays are ambiguous because the Hsp70 family of proteins is so complex. While there is some indication that Hsp70A and Grp70 are upregulated under conditions of stress, the significant basal level of the inducible Hsp70A protein in normal tissue, neoplastic tissue, and cell lines (Bachelet et al., *Cell Stress & Chaperones* 3:168–176, 1998; Bratton et al., *Int. J. Hyperthermia* 13:157–168, 1997; Sztankay et al., *Journal of Autoimmunity* 7:219–230, 1994), and an extreme variation in baseline levels in unstressed cells (Pockley et al., *Immunol. Invest.* 27:367–77, 1998), confounds interpretation limits the utility of previous studies. The dual function of the Hsp70 family is also problematic. Hsp70 stress proteins function both constitutively (by performing cellular "housekeeping" functions) and inductively (by responding to adverse changes to the cellular environment). The assays developed to date assess incremental increases in an already expressed protein (Hsp70A) but, because preexisting basal levels fluctuate so much, the results are difficult to interpret. Thus, there is a need for antibodies that specifically bind the strictly stress inducible Hsp70B' protein. The novel compositions of the present invention fulfill this need.

SUMMARY OF THE INVENTION

The present invention is based, in part, on the identification of immunogenic peptide sequences from the human Hsp70B protein. Antibodies that specifically bind this protein can be used to distinguish between the expression of HSC70/HSP70 proteins, which occurs while a cell is functioning normally and when it is responding to stress, and the Hsp70B' protein, which is only produced in response to stress (i.e., substances or events that are detrimental to the health of the cell or organism). Hsp70B' is unique among Hsp70 family proteins because neither hsp70B' mRNA nor Hsp70B' protein has been detected in unstressed cells. Accordingly, the present invention features compositions and methods for determining whether a cell (or a population of cells, such as those in cell culture or within a tissue) expresses Hsp70B'. A positive reaction to an Hsp70B' antibody not only provides evidence of stress in a particular cell, but also provides an indication of the general state of the health of the organism in which that cell resides (or from which it was obtained). As described below, the compositions of the invention (e.g. antibodies that specifically bind an Hsp70B' protein, an antigenic fragment, or an epitope thereof) can be used to determine whether a cell (e.g. a human cell), an organ (e.g. the skin or the liver), or an entire organism (e.g. a human) has been exposed to a stressor.

The invention also features peptides that correspond to, or are antigenically equivalent to, regions of the Hsp70B' protein. The peptide can consist of five or more (e.g., 5, 6, 7, 8, 10, or 12) consecutive amino acids from Hsp70B' protein (beginning at the second, fourth, sixth, or eighth residue), such as the following amino acid sequences: (1) VPGGSSCGTQARQGDPSTGPI (SEQ ID NO:1) (e.g., CGTQARQGDPSTGPI (SEQ ID NO:2) and CGTQAR-QGDPST (SEQ ID NO:3)); (2) RDKLPEEDRRKMQDKC (SEQ ID NO: 4) (e.g., RDKJPEEDRRKMQ (SEQ ID NO:5); when these peptides are linked to keyhole limpet hemocyanin (KLH), they can include cysteine residues); (3) AHVFHVKGSLQEESLRDKIPEEDRRKMQ (SEQ ID NO:6) (e.g., AHVFHVKGSLQEES (SEQ ID NO:7); (4) MQAPRELAVGID (SEQ ID NO:8), which is located in the N-terminal of Hsp70B' and, when linked to KLH includes a cysteine residue (i.e., MQAPRELAVGID(C) (SEQ ID NO.:9)); (5) GSLQEESLRDKIPEE (SEQ ID NO:10).

The peptides of the invention can contain at least one amino acid substitution (e.g., 1, 2, or 3 of the residues in the peptides of the invention can be replaced with another amino acid residue; alternatively, up to about 50% (e.g., 10%, 25%, 30%, 40% or 50%) of the residues in the peptides can be substituted). The substitution can constitute a conservative amino acid substitution. Conservative substitutions include interchanges of alanine and valine, valine and isoleucine, leucine and isoleucine, aspartic acid and glutamic acid, threonine and serine, and others of a similar nature (for example, any in which the neutral, positive or negative charge of the original amino acid residue is maintained). Conservative amino acid substitutions are well known to those of ordinary skill in the art. Preferably, peptides containing substitutions will be antigenically equivalent to the naturally occurring peptide sequence (i.e. a peptide containing a substitution will have a relative titre index that is no less than half as great as the relative titre index of the naturally occurring peptide). The peptides of the invention can also be attached to a carrier (e.g., KLH or ovalbumin) that enhances their immunogenicity or circulating half-life. Unless otherwise noted, a "protein" is a full-length protein (e.g, a full length Hsp70B' protein) and a "peptide" is a portion of a full-length protein (e.g. five or more consecutive amino acid residues present within the Hsp70B' protein). A "polypeptide" may be either a protein or peptide.

In related aspects, the invention features antibodies that specifically bind Hsp70B' or one of the Hsp70B' peptides disclosed herein and methods of obtaining those antibodies. The antibodies can be polyclonal or monoclonal antibodies, and can be produced by methods well known to those of ordinary skill in the art. These methods typically include immunizing an animal with Hsp70B' or an Hsp70B' peptide, but can be carried out instead by immunizing an animal with a nucleic acid molecule that encodes Hsp70B' or an Hsp70B' peptide.

The antibodies of the invention may be used to specifically bind, and thereby detect, Hsp70B' in virtually any immunoassay (e.g., an assay carried out by binding Hsp70B' proteins or peptides that are immobilized (e.g. on a membrane or column) or present in a cell (by, e.g., immunohistochemistry)). Accordingly, the invention features kits that include antibodies that specifically bind an Hsp70B' protein or peptide. The kits can also optionally include an Hsp70B' protein or peptide (as a positive control), an irrelevant protein (i.e., one to which the supplied antibody does not bind; as a negative control), secondary antibodies, other reagents, buffers, or solutions, and instructions.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 2 is a representation of the human Hsp70B' amino acid sequence (SEQ ID) NO:11).

DETAILED DESCRIPTION

Figure 1A:
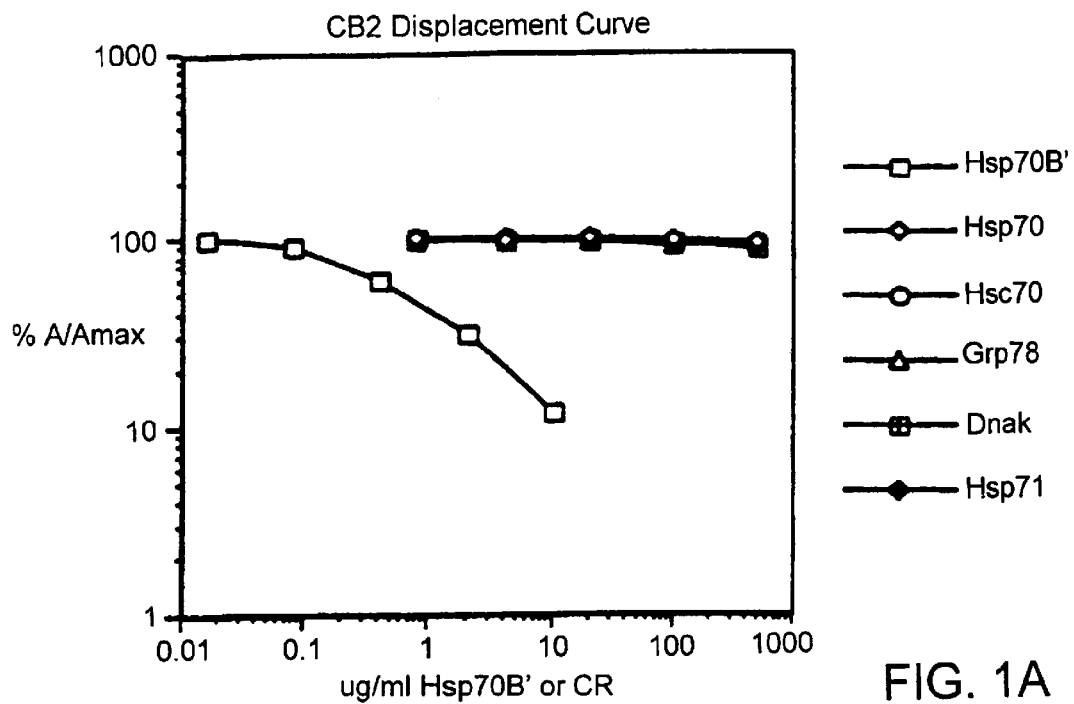
FIGS. 1A–1C are plots representing the displacement curves for Hsp70B' antibodies in the presence of Hsp70B' standard and HSP70 homologues. (1A) is the CB2 displacement curve, (1B) is the CD displacement curve, and (1C) is the 70B' WP displacement curve.

The invention features immunogenic peptides whose sequence is present in the Hsp70B' protein or whose sequence varies from the sequence of the Hsp70B' protein in such a limited way as to remain an antigenic equivalent of the naturally occurring peptide. For example, an Hsp70B' protein or peptide that contains one or more amino acid substitutions (e.g. one or more conservative amino acid substitutions) can be antigenically equivalent to the naturally occurring Hsp70B' protein or peptide fragments thereof. Proteins and peptides that, upon administration to an animal, elicit the production of antibodies that specifically bind to Hsp70B' protein include the following: (1) VPGGSS-CGTQARQGDPSTGPI (SEQ ID NO.1) (e.g., CGTQAR-QGDPSTGPI (SEQ ID NO:2) and CGTQARQGDPST (SEQ ID NO: 3)); (2) RDKIPEEDRRKMQDKC (SEQ ID NO.4) (e.g., RDKIPEEDRRKMQ (SEQ ID NO:5); when these peptides are linked to keyhole limpet hemocyanin (KLH), they can include N-terminal cysteine residues); (3) AHVFHVKGSLQEESLRDKIPEEDRRKMQ (SEQ ID NO:6) (e.g. AHVFHVKGSLQEES (SEQ ID NO;7); (4) MQAPRELAVGID (SEQ ID NO:8), which is located in the N-tenninal of Hsp70B' and, when linked to KLH includes a C-terminal cysteine residue (i.e., MQAPRELAVGID(C) (SEQ ID NO:9)); (5) GSLQEESLRDKIPEE (SEQ ID NO:10); and the Hsp70B' protein (SEQ ID NO:11).

Portions of any of these peptides can also be used to generate Hsp70B'-specific antibodies. More specifically, five or more consecutive amino acid residues (i.e., amino acid residues linked to one another by peptide bonds in the same sequential order as they appear in the naturally occurring sequence) can be used. The starting point can be anywhere within the sequence of Hsp70B' or the Hsp70B' peptides disclosed herein, up to the fifth-to-last amino acid residue. Peptides based on the sequences disclosed herein can contain at least 5, 6, 7, 8, 9, 10, 11, 12, 13, 14, 15, 18, 20, 25, or 28 consecutive amino acid residues. Moreover, they can begin at, for example, the second, fifth, ninth, tenth, or twelth residue in any of the peptides disclosed herein.

The Hsp70B' protein or any of the Hsp70B' peptides can be attached to a carrier that enhances their immunogenicity. The carrier is any substance that, when attached to the protein or peptide, results in the production of more antibodies than when it is omitted from the protein or peptide. The carrier can be attached to the protein or peptide covalently or noncovalently so long as the two entities remain attached to one another when administered to an animal. More specifically, the carrier can be an amino acid-based substance such as keyhole limpet hemocyanin (KLH). Regardless of the means of attachment, one or more groups (e.g., chemically reactive groups or one or more amino acid residues) can be used to facilitate bonding between the protein or peptide and the carrier. For example, a cysteine residue can be added to either end of Hsp70B' or to any of the Hsp70B' peptides described herein to facilitate coupling with a carrier. If desired, more than one carrier can be used, and a spacer (e.g. one or more amino acid residues) can be added between the protein or peptide and the carrier.

Antibodies may generally be prepared by any of a variety of techniques known to those of ordinary skill in the art (see, e.g., Harlow and Lane, *Antibodies. A Laboratory Manual*, Cold Spring Harbor Laboratory, 1988). For example, an immunogen that includes a Hsp70B' peptide is initially injected into suitable animals (e.g., mice, rats, rabbits, sheep and goats) according to a predetermined schedule with one or more booster immunizations, and blood samples are obtained from the animals periodically. Polyclonal antibodies specific for the Hsp70B' peptide can then be purified from the antisera by, for example, affinity chromatography in which the same peptide sequence administered is coupled to a suitable solid support.

To obtain Hsp70B'-specific antibodies, an animal can be immunized with Hsp70B' or one of the Hsp70B' peptides disclosed herein. The term "immunized" refers to at least a first administration of antigen, and optionally includes subsequent administration (e.g., a second or third administration) and additional periodic boosting. Immunization typically includes administration of the antigen (i.e. an Hsp70B' protein or a fragment or epitope thereof that evokes an immune response) and an adjuvant. The Hsp70B' protein or peptide administered can be purified from a natural source, chemically synthesized, or recombinantly produced. Regardless of the length of the amino acid sequence used to immunize an animal, sera (or antigen-specific B cells or other antibody containing fluids) are collected, and the antibody response is evaluated, typically by immunoassay. High-titre preparations are generally pooled and the protein-specific or peptide-specific antibody is purified on an immunoaffinity column to which the protein or peptide is immobilized. Where full length Hsp70B' protein (or any portion of the protein that is longer than the peptides disclosed herein) is used to generate antibodies by immunization or otherwise, an Hsp70B' peptide (such as those disclosed herein) is typically used to purify the antibodies. The discovery of amino acid sequences within Hsp70B' that can yield antibodies that distinguish Hsp70B' from other Hsp70 family members permits antibodies to be obtained in many ways known to those of ordinary skill in the art.

In addition to polyclonal antibodies, the antibodies generated can be monoclonal antibodies, fragments of polyclonal or monoclonal antibodies such as F(ab')$_2$, and Fab fragments, as well as any naturally occurring or recombinantly produced binding partners (i.e., molecules that specifically bind Hsp70B'). In addition to the Hsp70B' protein or peptide (which functions as an antigen), the composition administered can include a carrier vehicle and immunostimulatory substances that enhance immunogenicity (e.g., adjuvants). The carrier vehicle can include aluminum salts, water-in-oil emulsions, biodegradable oil vehicles, oil-in-water emulsions, biodegradable microcapsules, and liposomes. The immunostimulatory substances can include N-acetylmuramyl-L-alanine-D-isoglutamine (MDP), lipopoly-saccharides (LPS), glucan, IL-12, GM-CSF, gamma interferon, and IL-15.

Monoclonal antibodies specific for Hsp70B' peptides can be prepared, for example, using the technique of Kohler and Milstein (*Eur. J. Immunol.* 6:511–519, 1976), and improvements thereto. Briefly, these methods involve the preparation of immortal cell lines that produce antibodies having the desired specificity (i.e., reactivity with the Hsp70B' peptide of interest). Such cell lines may be produced, for example, from spleen cells obtained from an immunized animal. The spleen cells are then immortalized by, for example, fusion with a myeloma cell fusion partner, preferably one that is syngeneic with the immunized animal. For example, the spleen cells and myeloma cells may be combined with an agent that promotes membrane fusion (e.g., polyethylene glycol or a nonionic detergent), and then plated at low density on a selective medium that supports the growth of hybrid cells, but not myeloma cells. The selection technique can be HAT (hypoxanthine, aminopterin, thymidine) selection. After a sufficient time (typically 1 to 2 weeks), colonies of hybrids are observed. Single colonies are selected and tested for binding activity against the polypeptide. Hybridomas having high reactivity and specificity are preferred. Monoclonal antibodies may be isolated from the supernatants of growing hybridoma colonies. Accordingly, such hybridomas and the monoclonal antibodies they produce (i.e., monoclonal antibodies that specifically bind to Hsp70B' or Hsp70B' peptides) are specifically encompassed by the present invention.

Techniques that enhance the yield of antibodies are known in the art and can be used in the context of the present invention. For example, the hybridoma cell line can be injected into the peritoneal cavity of a suitable vertebrate host, such as a mouse, and monoclonal antibodies may then be harvested from the ascites fluid or the blood of that host. Contaminants can be removed by conventional techniques, such as chromatography, gel filtration, precipitation, and extraction. For example, anti-Hsp70B' antibodies can be purified by chromatography on immobilized Protein G or Protein A using standard techniques.

Instead of administering Hsp70B' or Hsp70B' peptides, animals can be indirectly immunized by administering nucleic acid molecules encoding Hsp70B' or a Hsp70B' peptide. Accordingly, nucleic acid molecules that encode the Hsp70B' peptides disclosed herein, alone or in the context of an expression, and cells that contain those molecules are within the scope of the invention. These nucleic acid molecules can be delivered with recombinant viral vectors (e.g., retroviruses (see WO 90/07936, WO 91/02805, WO 93/25234, WO 93/25698, and WO 94/03622), adenovirus (see Berkner, *Biotechniques* 6:616–627, 1988; Li et al., *Hum. Gene Ther.* 4:403–409, 1993; Vincent et al., *Nat. Genet.* 5:130–134, 1993; and Kolls et al., *Proc. Natl. Acad. Sci. USA* 91:215–219, 1994), pox virus (see U.S. Pat. Nos. 4,769,330 and 5,017,487; and WO 89/01973)), naked DNA (see WO 90/11092), nucleic acid molecule complexed to a polycationic molecule (see WO 93/03709), and nucleic acid associated with liposomes (see Wang et al., *Proc. Natl. Acad. Sci. USA* 84:7851, 1987). The DNA can be linked to killed or inactivated adenovirus (see Curiel et al., *Hum. Gene Ther.* 3:147–154, 1992; Cotton et al., *Proc. Natl. Acad. Sci. USA* 89:6094, 1992). Other suitable compositions include DNA-ligand (see Wu et al., *J. Biol. Chem.* 264:16985–16987, 1989) and lipid-DNA combinations (see Felgner et al., *Proc. Natl. Acad. Sci. USA* 84:7413–7417, 1989). In addition, the efficiency with which naked DNA is taken up by cells can be increased by coating the DNA onto biodegradable beads.

In some cases, antigen-binding fragments of antibodies are preferred. These fragments include Fab fragments, which may be prepared using standard techniques (e.g., by digestion with papain to yield Fab and Fc fragments). The Fab and Fe fragments can be separated by affinity chromatography (e.g., on immobilized protein A columns), using standard techniques. See, e.g., Weir, D. M., *Handbook of Experimental Immunology,* 1986, Blackwell Scientific, Boston.

Multifunctional fusion proteins having specific binding affinities for pre-selected antigens by virtue of immunoglobulin V-region domains encoded by DNA sequences linked in-frame to sequences encoding various effector proteins are known in the art, for example, as disclosed in EP-B1-0318554 and U.S. Pat. Nos. 5,132,405 and 5,091,513, and 5,476,786. Such effector proteins include polypeptide domains that can be used to detect binding of the fusion protein by any of a variety of routinely practiced techniques, including but not limited to a biotin mimetic sequence (see, e.g., Luo et al., *J. Biotechnol.* 65:225, 1998 and references cited therein), direct covalent modification with a detectable labeling moiety, non-covalent binding to a specific labeled reporter molecule, enzymatic modification of a detectable substrate or immobilization (covalent or non-covalent) on a solid-phase support.

Single chain antibodies that can be used in the methods described herein can also be generated and selected by a method such as phage display (see, e.g., U.S. Pat. No. 5,223,409, Schlebusch et al., *Hybridoma* 16:47,1997, and references cited therein). Briefly, in this method, DNA sequences are inserted into the gene III or gene VIII gene of a filamentous phage, such as M13. Several vectors with multicloning sites have been developed for insertion (McLafferty et al., *Gene* 128:29–36, 1993; Scott and Smith, *Science* 249:386–390, 1990; Smith and Scott, *Methods Enzymol.* 217:228–257, 1993). The inserted DNA sequences can be randomly generated or can be variants of a known binding domain for binding to Hsp70B' peptides. Single chain antibodies can be readily generated using this method. Generally, the inserts encode from 5 to 20 amino acid residues. The peptide encoded by the inserted sequence is displayed on the surface of the bacteriophage. Bacteriophage expressing a binding domain for a Hsp70B' peptide are selected by binding to an immobilized Hsp70B' peptide, for example a recombinant polypeptide prepared using methods well known in the art and nucleic acid coding sequences as disclosed by Chang et al. (*Proc. Nat. Acad. Sci. USA* 93:136, 1996) or by Kojima et al. (*J. Biol. Chem.* 270:21984, 1995). Unbound phage is removed by a wash, typically containing 10 mM Tris, 1 mM EDTA, and without salt or with a low salt concentration. Bound phage is eluted with a salt containing buffer, for example. The NaCl concentration is increased in a step-wise fashion until all the phage is eluted. Typically, phage binding with higher affinity will be released by higher salt concentrations. Eluted phage is propagated in the bacteria host. Further rounds of selection may be performed to select for a few phage binding with high affinity. The DNA sequence of the insert in the binding phage is then determined. Once the predicted amino acid sequence of the binding peptide is known, sufficient peptide for use as an antibody specific for a human Hsp70B' protein or peptide can be made either by recombinant means or synthetically. Recombinant means are used when the antibody is produced as a fusion protein. The peptide can also be generated as a tandem array of two or more similar or dissimilar peptides, in order to maximize affinity or binding.

Antibodies that specifically bind an Hsp70B' protein (e.g., a murine, porcine, bovine, equine, or human Hsp70B' protein) can be used in vitro or in vivo to evaluate, diagnose, or form a prognosis regarding a specific cell or a disease state. These antibodies are molecular markers of exposure to a stressful environment (e.g. an environment where the temperature is increased beyond physiological norms, there is a shortage of oxygen, or an infectious organism) or substance (e.g. a toxin, a proinflammatory cytokine, a heavy metal, an amino acid analogue, or a metabolic poison). Notably, the antibodies can serve as markers of an adverse sub-lethal effect of stress. To detect an antigenic determinant reactive with an antibody specific for a human Hsp70B' peptide, the detection reagent is typically an antibody, which may be prepared as described herein. The variety of assay formats known to those of ordinary skill in the art include, but are not limited to, enzyme immunoassay (EIA), enzyme linked immunosorbent assay (ELISA), radioimmunoassay (RIA), immunofluorimetry, immunoprecipitation, equilibrium dialysis, immunodiffusion and other techniques. See, e.g., Harlow and Lane, *Antibodies. A Laboratory Manual,* Cold Spring Harbor Laboratory, 1988; Weir, D. M., *Handbook of Experimental Immunology,* 1986, Blackwell Scientific, Boston. For example, the assay may be performed in a Western blot format in which a protein preparation from the biological sample is subjected to gel electrophoresis, transferred to a suitable membrane, and allowed to react with the antibody. The presence of the antibody can then be detected using a suitable detection reagent, as is well known in the art and described below.

The assay can also involve antibodies immobilized on a solid support (e.g., a test well in a microtiter plate, a nitrocellulose filter or other suitable membrane, a bead or disc, such as glass, fiberglass, latex or a plastic such as polystyrene or polyvinylchloride). The immobilized antibody can bind to the target Hsp70B' peptide or protein and thereby separate it from substantially all of the rest of the sample. The bound polypeptide can then be detected with a second antibody reactive with a distinct polypeptide antigenic determinant, for example, a reagent that contains a detectable reporter moiety. For example, the immobilized antibody and the secondary antibody which each recognize distinct antigenic determinants may be two monoclonal antibodies. Alternatively, a competitive assay may be utilized, in which a polypeptide is labeled with a detectable reporter moiety and allowed to bind to the immobilized polypeptide specific antibody after incubation of the immobilized antibody with the sample. The extent to which components of the sample inhibit the binding of the labeled polypeptide to the antibody is indicative of the reactivity of the sample with the immobilized antibody, and as a result, indicative of the level of Hsp70B' polypeptide in the sample.

In some cases, the assay used to detect Hsp70B' polypeptides in a sample is a two-antibody sandwich assay. This assay can be performed by first contacting a Hsp70B' antibody that has been immobilized on a solid support (commonly the well of a microtiter plate) with the biological sample. Soluble molecules that naturally occur in the sample and have an antigenic determinant that is reactive with the antibody will bind to the immobilized antibody and thereby form an antigen-antibody complex or an immune complex. A 30-minute incubation at room temperature is generally sufficient for complex formation. Unbound constituents of the sample are then removed from the immobilized immune complexes and a second antibody specific for a Hsp70B' polypeptide is added. The antigen-combining site of the second antibody does not competitively inhibit binding of the antigen-combining site of the immobilized first antibody. The second antibody may be detectably labeled as provided herein, such that it may be directly detected. Alternatively, the second antibody may be indirectly detected with a labeled secondary (or "second stage") anti-antibody, or by using a specific detection reagent as provided herein. Notably, the methods of the invention need not be limited to any particular detection procedure. Those familiar with immunoassays understand that there are numerous reagents and configurations for immunologically detecting a particular antigen in a two-antibody sandwich immunoassay.

When a two-antibody sandwich assay is used, the first, immobilized antibody specific for a Hsp70B' polypeptide and the second antibody specific for a Hsp70B' polypeptide can both be polyclonal antibodies. Alternatively, the first, immobilized antibody specific for Hsp70B' polypeptide can be a monoclonal antibody and the second antibody specific for a Hsp70B' polypeptide can be a polyclonal antibody and vice-versa. It can be preferable, however, to carry out the assay with the first, immobilized antibody and the second anti-Hsp70B' antibody being monoclonal antibodies. In yet other configurations, the first, immobilized antibody and/or the second antibody may be any of the kinds of antibodies known in the art (for example, Fab fragments, F(ab')$_2$ fragments, immunoglobulin V-region fusion proteins or single chain antibodies). Those of ordinary skill in the art will appreciate that the present invention can be practiced with other antibody forms, fragments, derivatives, and the like.

The second antibody may contain a detectable reporter moiety or label such as an enzyme, dye, radionuclide, luminescent group, fluorescent group or biotin, or the like. The amount of the second antibody that remains bound to the solid support is then determined using a method appropriate for the specific detectable reporter moiety or label. For radioactive groups, scintillation counting or autoradiographic methods are generally appropriate. Antibody-enzyme conjugates may be prepared using a variety of coupling techniques (for review see, e.g., Scouten, W. H., *Methods in Enzymology* 135:30–65, 1987). Spectroscopic methods may be used to detect dyes (including, for example, calorimetric products of enzyme reactions), luminescent groups and fluorescent groups. Biotin may be detected using avidin or streptavidin, coupled to a different reporter group (commonly a radioactive or fluorescent group or an enzyme). Enzyme reporter groups may generally be detected by the addition of substrate (generally for a specific period of time), followed by spectroscopic, spectrophotometric or other analysis of the reaction products. Standards and standard additions may be used to determine the level of Hsp70B' polypeptide in a sample, using well known techniques.

As noted above, the ability to generate anti-Hsp70B' antibodies to defined epitopes permits a variety of in vitro and in vivo uses. For example, anti-Hsp70B' antibodies may be used to monitor the protein levels of a specific, sensitive, native, biomarker (Hsp70B') in in vitro bioassays using human cell lines to evaluate the toxicity of chemical compounds. Using antibodies to defined epitopes on the Hsp70B' and Hsp70B proteins allows the specific monitoring of these proteins. Other uses include the evaluation, diagnosis, prognosis and continued monitoring of specific disease conditions such as: hypertension, oncology, organ transplantation, ischaemia and trauma, infection inflammation and fever, heart disease, autoimmune disorders, neurodegenerative diseases, monitoring spinal cord injuries, neuro-psychology evaluations, and chronic disease states.

An advantage of the present approach is that one can monitor perturbations in homeostasis by monitoring the levels of Hsp70B' in vivo. The Hsp70B' protein can also be used as a biomarker in the fields of organ transplantation and cytoprotection. This would allow one to identify physiological perturbations even when an individual has not received a definitive diagnosis with respect to a specific condition or to monitor patients exhibiting symptoms of known or unknown cause (e.g., chronic fatigue syndrome). Such monitoring would help healthcare professionals gauge the severity of a condition, follow the progress of the patient, and decide when intervention may be needed. Evaluating a stress response (made manifest by Hsp70B' expression) may also be useful in the care of patients who are in remission from an autoimmune, chronic condition or neoplasia; to evaluate amniotic fluids or samples of the placenta; and to assess newborn infants who are at risk (due, for example, to premature birth). Monitoring Hsp70B' is also useful in evaluating the fitness of healthy individuals (e.g., it can be used to assess training programs for high performance athletes). In yet other applications, the compositions and methods of the invention can be used to evaluate the ability of various therapeutic compounds to oppose the stress condition, and in conjunction with in vivo diagnostic imaging (e.g., to evaluate wounding, inflammation or pathology in patients).

The following examples illustrate, not limit, the invention.

EXAMPLES

The following materials were obtained from the commercial suppliers indicated: anisole (Cat. No. A4405, Sigma Chemical Co., herein "Sigma", St. Louis, Mo.); 2,2'-azino-di-(3-ethyl-benzthiazoline-sulfonic acid) (ABTS) (Cat. No. A6499, Molecular Probes Eugene, Oreg.); activated Maleimide Keyhole Limpet Cyanin (Cat. No. 77106, Pierce Chemical Co. Rockford, Ill.); Biotin (Cat. No. B2643, Sigma); boric acid (Cat. No. B0252, Sigma); Sepharose® 4B (Cat. No. 17-0120-01, LKB/Pharmacia, Uppsala, Sweden); bovine serum albumin (LP) (Cat. No. 100 350, Boehringer Mannheim, Indianapolis, Ind.); cyanogen bromide (Cat. No. C6388, Sigma, St. Louis, Mo.); dialysis tubing Spectra/Por™ membrane MWCO: 6-8,000 (Cat. No. 132 665, Spectrum Industries Inc., Laguna Hills, Calif.); dimethyl formamide (DMF) (Cat. No. 22705-6, Aldrich Chemical Company, Milwaukee, Wis.); DIC (Cat. No. BP 592-500, Fisher); ethanedithiol (Cat. No. 39,802-0, Aldrich Chemicals, Milwaukee, Wis.); ether (Cat. No. TX 1275-3, EM Sciences); ethylenediaminetetraacetatic acid (EDTA) (Cat No. BP 120-1, Fisher Scientific, Springfield, N.J.); 1-ethyl-3-(3' dimethylaminopropyl)-carbodiimide, HCL (EDC) (Cat No. 341-006, Calbiochem, San Diego, Calif.); freund's adjuvant, complete (Cat. No. M-0638-50B, Lee Laboratories, Grayson, Ga.); freund's adjuvant, incomplete (Cat. No. M0639-50B, Lee Laboratories); fritted chromatography columns (Column part No. 12131011; Frit: Part No. 12131029, Varian Sample Preparation Products, Harbor City, Calif.); gelatin from bovine skin (Cat. No. G9382, Sigma); glycine (Cat. No. BP381-5, Fisher); goat anti-rabbit IgG, biotinylated (Cat No. A 0418, Sigma); HOBt (Cat. No. 01-62-0008, Calbiochem-Novabiochem); horseradish peroxidase (HRP) (Cat. No. 814 393, Boehringer Mannheim); HRP-Streptavidin (Cat. No. S 5512, Sigma); hydrochloric acid (Cat No. 71445-500, Fisher); hydrogen peroxide 30% w/w (Cat. No. H1009, Sigma); methanol (Cat. No. A412-20, Fisher); microtitre plates, 96 well (Cat. No. 2595, Corning-Costar Pleasanton, Calif.); N-α-Fmoc protected amino acids (Calbiochem-Novabiochem, San Diego, Calif.; see 1997–1998 catalog pages 1–45); N-α-Fmoc protected amino acids attached to Wang Resin (Calbiochem-Novabiochem;

see 1997–1998 catalog pages 161–164); NMP (Cat. No. CAS 872-50-4, Burdick and Jackson, Muskegon, Mich.); peptide (Synthesized by Research Genetics, Inc., see below); piperidine (Cat. No. 80640, Fluka, available through Sigma); sodium bicarbonate (Cat. No. BP328-1, Fisher); sodium borate (Cat. No. B9876, Sigma); sodium carbonate (Cat. No. BP357-1, Fisher); sodium chloride (Cat. No. BP 358-10, Fisher); sodium hydroxide (Cat. No. SS 255-1, Fisher); streptavidin (Cat. No. 1 520, Boehringer Mannheim); thioanisole (Cat. No. T-2765, Sigma); trifluoroacetic acid (Cat. No. TX 1275-3, EM Sciences); Tween-20 (Cat. No. BP 337-500, Fisher); and Wetbox-(Rubbermaid Rectangular Servin' Saver™ Part No. 3862 Wooster, Ohio).

The following general solutions were prepared: (1) BBS—Borate Buffered Saline with EDTA dissolved in distilled water (pH 8.2 to 8.4 with HCl or NaOH), which contains 25 mM Sodium borate (Borax), 100 mM Boric Acid, 75 mM NaCl, and 5 mM EDTA; (2) 0.1 N HCl in saline, which contains concentrated HCl (8.3 mL/0.917 L distilled water) and 0.154 M NaCl; (3) Glycine (pH 2.0 and pH 3.0) dissolved in distilled water and adjusted to the desired pH, which contains 0.1 M glycine and 0.154 M NaCl; (4) 5× Borate 1× Sodium Chloride dissolved in distilled water, which contains 0.11 M NaCl, 60 mM sodium borate, and 250 mM boric acid; and (5) substrate buffer in distilled water adjusted to pH 4.0 with sodium hydroxide, which contains 50 to 100 mM Citric Acid.

The following peptide synthesis solutions were prepared: (1) AA solution, in which HOBt is dissolved in NMP (8.8 grams HOBt to 1 liter NMP) and Fmoc-N-a-amino is added at a concentration at 0.53 M; (2) DIC solution, which is 1 part DIC to 3 parts NMP; (3) a deprotecting solution, which is 1 part piperidine and 3 parts DMF; and (4) Reagent R, which is 2 parts anisole, 3 parts ethanedithiol, 5 parts thioanisole, and 90 parts trifluoroacetic acid.

The following equipment was employed: an MRX plate reader (Dynatech Inc., Chantilly, Va.); a Hamilton Eclipse (Hamilton Instruments, Reno, Nev.); a Beckman TJ-6 centrifuge, refrigerated (Model No. TJ-6, Beclman Instruments, Fullerton, Calif.); a Chart Recorder (Recorder 1 Part No. 18-1001-40, Pharmacia LKB Biotechnology); a UV monitor (Uvicord SII Part No. 18-1004-50, Pharmacia LKB Biotechnology); an Amicon Stirred Cell Concentrator (Model 8400, Amicon Inc., Beverly, Mass.); 30 kDa MW cut-off filters (Cat. No. YM-30 Membranes Cat. No. 13742, Amicon Inc., Beverly, Mass.); a multi-channel automated pipettor (Cat. No. 4880, Corning Costar Inc., Cambridge, Mass.); a pH meter (Corning 240; Corning Science Products, Corning Glassworks, Corning, N.Y.); an ACT396 peptide synthesizer (Advanced ChemTech, Louisville, Ky.); a vacuum dryer (Box is from Labconco, Kansas City, Mo.; Pump is from Alcatel, Laurel MD); a lyophilizer (Unitop 600sl in tandem with Freezemobile 12, both from Virtis, Gardiner, N.Y.).

Methods: Hsp70B' Antibodies were produced as follows. Hsp70B' antibodies were produced in rabbits, goats and mice with either synthetic peptides or recombinant Hsp70B' protein as immunogen. Eight peptides were chosen from the human Hsp70B' amino acid sequence. One of the Hsp70B' peptides, the NT peptide MQAPRELAVGID(C) (SEQ ID NO:9) corresponded to an N-terminal fragment. The other seven fragments were derived from the C-terminal half of the Hsp70B' protein and included the CC peptide (AHVFHVKGSLQEES; (SEQ ID NO:7), the CA peptide (RDKIPEEDRRKMQ; (SEQ ID NO:5), the CD peptide (RDKIPEEDRRKMQDKC; (SEQ ID NO:4), the GB peptide (CGTQARQGDPSTGPI; (SEQ ID NO:2), the ECB peptide (VPGGSSCGTQARQGDPSTGPI; (SEQ ID NO:1), the TCB peptide (CGTQARQGDPST; (SEQ ID NO:3), and the CE peptide (GSLQEESLRDKIPEE; (SEQ ID NO:10). The GB peptide was also resynthesized on a separate occasion and designated CB2. All peptides were chemically coupled to KLH and animals were immunized with the peptide conjugates. Recombinant human Hsp70B' protein was purified to ~90% homogeneity and was also used as an immunogen. Primary immunizations were administered in Freund's complete adjuvant and subsequent boosts were made in Freund's incomplete adjuvant. Animals were immunized and boosted on a monthly basis. Sera were collected at various time points and the antibody response to the immunizing protein or peptide was evaluated in an indirect enzyme immunoassay (EIA). Titres were established as the dilution factor at which the absorbance in the test sample was equal to 0.2 optical density units. In some instances, high-titre antisera from each set of animals were pooled and the antigen-specific antibody purified on peptide immunoaffinity columns.

Peptide was synthesized as follows. The event procedures included an incubation step (which allowed resin to be immersed in an appropriate solution; all incubation steps occurred with mixing, a wash (addition of 2 mls of DMF, incubation for 5 minutes and removal of the wash solution), and a wash cycle (consisting of 5 washes). For machine synthesis, sequences of peptide were added to the peptide synthesizer. The C-terminal residue was determined and the appropriate Wang Resin was attached to the reaction vessel. The peptides were synthesized from the C-terminus to the N-terminus by adding one amino acid at a time during the synthesis cycles. The amino acid residue selected for addition to the peptide is controlled by sequence of the peptide that was entered into the database of the synthesizer.

The synthesis per se included a first step in which resin swelled (2 ml of DMF was added for 30 minutes and then removed), a second step in which the peptide was deprotected (1 ml deprotecting solution is added to the reaction vessel and incubated for 20 minutes), washed, and coupled (750 ml of amino acid solution and 250 ml of DIC solution are added to the reaction vessel for 30 minutes and then washed out. The coupling step is repeated once before another wash cycle. The second step is repeated over the length of the peptide, with the amino acid solution changing as the sequence listed in the peptide synthesizer's database dictates. In a third step, final deprotection occurs (the deprotection and washing that occurs during the synthesis cycle are performed one last time). Resins are deswelled in methanol by two rinses with 5 ml methanol, a 5 minute incubation in 5 ml methanol, and a rinse in 5 mL methanol, and then vacuum dried.

Peptide was removed from the resin by incubation for 2 hours in reagent R and then precipitated into ether. The peptide was then washed in ether, vacuum dried, resolubilized in diH$_2$O, frozen, and lyophilized overnight. At this point, the peptide can be conjugated to KLH as follows. The peptide (6 mg) is dissolved in PBS (6 ml) and mixed with 6 mg of maleiimide activated KLH carrier in 6 ml of PBS for a total volume of 12 mL. The entire solution was mixed for two hours, dialyzed in 1 liter of PBS, and lyophilized.

Animals were immunized with peptide conjugates as follows. Three New Zealand White rabbits were injected in three to four subcutaneous dorsal sites with 250 μg of peptide-KLH conjugate in Freund's complete adjuvant. Booster shots (100 μg) were administered in Freund's incomplete adjuvant. The total volume of each injection was 1 ml.

The rabbit immunization schedule was as follows: at Day 0 a "pre-immune bleed" was performed and the primary immunization was given; at week 2 a first booster was given; at week 4 a blood sample was obtained; at week 6 a second booster was given; at week 8 a second blood sample was obtained and a third booster was given; at week 10 a third blood sample was obtained; at week 12 a fourth booster was given; and at week 14 a fourth and final blood sample was obtained.

Goats were injected with the same dose of peptide conjugate in Freund's adjuvant as the rabbits received. The immunization schedule was also the same except the booster at week 12 was not given and no blood sample was taken at week 14.

BALB/c mice were immunized intraperitoneally with 50 μg peptide conjugate in Freund's complete adjuvant on day 0, and in Freund's incomplete adjuvant at weeks 2, 5 and 8. Mouse test bleeds were collected on week 7 and 10.

Rabbits were also immunized with recombinant human Hsp70B' protein. More specifically, three New Zealand White rabbits were immunized on day 0 with purified recombinant human Hsp70B' protein in Freund's complete adjuvant. Booster shots (100 μg) were given at weeks 3, 4, 6, and 8, and blood samples were collected at weeks 5, 7, 9 and 10. The blood samples were processed for serum, and the antibody obtained was designated 70B' WP.

To collect rabbit serum, the rabbits were bled (30 to 50 ml) from the auricular artery. The blood was allowed to clot at room temperature for 15 minutes and the serum was separated from the clot using an IEC DPR-6000 centrifuge at 5000×g. Cell-free serum was decanted gently into a clean test tube and stored at −20° C. for affinity purification.

Anti-peptide titre was determined as follows. All solutions were added by a liquid handling dispenser (the Hamilton Eclipse), with the exception of the wash solution. The anti-peptide titres in the rabbits, goats, and mice were determined in an ELISA with peptide on the solid phase. Flexible high binding ELISA plates were passively coated with peptide diluted in BBS (100 μL, 1 μg/well) and the plate was incubated at 4° C. in a wetbox overnight (air-tight container with moistened cotton balls). The plates were emptied and then washed three times with BBS containing 0.1% Tween-20 (BBS-TW) by repeated filling and emptying using a semi-automated plate washer. The plates were blocked by completely filling each well with BBS-TW containing 1% BSA and 0.1% gelatin (BBS-TW-BG) and incubating for 2 hours at room temperature. The plates were emptied and sera of both pre- and post-immune serum were added to wells. The first well contained sera at 1:50 in BBS. The sera were then serially titrated eleven more times across the plate at a ratio of 1:1 for a final (twelfth) dilution of 1:204,800. The plates were incubated overnight at 4° C. The plates were emptied and washed three times as described.

Biotinylated secondary antibodies (100 μl) were added to each microtitre plate test well and incubated for four hours at room temperature. The plates were emptied and washed three times. Horseradish peroxidase-conjugated Streptavidin (100 μL diluted 1:10,000 in BBS-TW-BG) was added to each well and incubated for two hours at room temperature. The plates were emptied and washed three times. The ABTS was prepared fresh from stock by combining 10 mL of citrate buffer (0.1 M at pH 4.0), 0.2 mL of the stock solution (15 mg/mL in water) and 10 μL of 30% $H_2O_2$. The ABTS solution (100 μL) was added to each well and incubated at room temperature. The plates were read at 414 λ, 20 minutes following the addition of substrate. Titres were established as the reciprocal dilution factor at which the test sample was equal to 0.2 absorbance units.

The Anti-Hsp70B' protein titre was determined by indirect ELISA with Hsp70B' on the solid phase. Nunc Maxisorp ELISA plates were passively coated with purified recombinant human Hsp70B' diluted in PBS (100 μl, 100 ng/well) at 4° C. overnight. Plates were washed six times with PBS containing 0.05% tween-20 (Bio-Rad) and then blocked at room temperature with 200 μl/well blotto (5% non-fat milk (Carnation), 0.05% tween-20, 0.02% thimerosal (Fisher Scientific) in PBS). Plates were washed and the antiserum, diluted 1:1000 in blotto, was added to the wells. The diluted antiserum was serially titrated 5 times at a ratio of 1:3 in blotto for a final dilution of 1:243000. Plates were incubated at room temperature for 1 hour, followed by washing as described. Peroxidase conjugated anti-rabbit IgG (100 μl/well of SAB-300, Stressgen Biotechnologies), diluted 1:25000 in blotto, was added to the wells and the plates were incubated for 1 hour at room temperature. Plates were washed as described and then developed with tetramethylbenzidine (TMB; BioFx) for 5–10 minutes at room temperature. Color development was stopped by the addition of acid stop solution (BioFx). Absorbance of each well was measured at 450 nm in an EL808 microplate reader (BioTek), interfaced with KC3 software. Titres were established as the reciprocal dilution factor at which the test sample was equal to 0.2 absorbance units.

The peptide affinity purification column was prepared by conjugating 5 mg of peptide to 10 ml of cyanogen bromide-activated Sepharose 4B, and 5 mg of peptide to hydrazine-Sepharose 4B. Briefly, 100 uL of DMF was added to peptide (5 mg) and the mixture was vortexed until the contents were completely wetted. Water was then added (900 μL) and the contents were vortexed until the peptide dissolved. Half of the dissolved peptide (500 μL) was added to separate tubes containing 10 mL of cyanogen-bromide activated Sepharose 4B in 0.1 mL of borate buffered saline at pH 8.4 (BBS), and 10 mL of hydrazine-Sepharose 4B in 0.1 M carbonate buffer adjusted to pH 4.5 using excess EDC in citrate buffer pH 6.0. The conjugation reactions were allowed to proceed overnight at room temperature. The conjugated Sepharose was pooled and loaded onto fritted columns, washed with 10 mL of BBS, blocked with 10 mL of 1 M glycine, and washed with 10 mL 0.1 M glycine adjusted to pH 2.5 with HCl and re-neutralized in BBS. The column was washed with enough volume for the optical density at 280 λ to reach baseline.

To affinity purify antibodies, the peptide affinity column was attached to a UV monitor and chart recorder. The titred rabbit antiserum was thawed and pooled. The serum was diluted with one volume of BBS and allowed to flow through the columns at 10 mL per minute. The non-peptide immunoglobulins and other proteins were washed from the column with excess BBS until the optical density at 280 λ reached baseline. The columns were disconnected and the affinity purified column was eluted using a stepwise pH gradient from pH 7.0 to pH 1.0. The elution was monitored at 280 nM, and fractions containing antibody (pH 3.0 to pH 1.0) were collected directly into excess 0.5 M BBS. Excess buffer (0.5 M BBS) in the collection tubes served to neutralize the antibodies collected in the acidic fractions of the pH gradient.

The entire procedure was repeated with "depleted" serum to ensure maximal recovery of antibodies. The eluted material was concentrated using a stirred cell apparatus and a membrane with a molecular weight cutoff of 30 kD. The concentration of the final preparation was determined using an optical density reading at 280 nM. The concentration was determined using the following formula: mg/mL=$OD_{280}$/1.4.

Antibody titres were determined by indirect EIA, essentially as already described for the anti-peptide and anti-Hsp70B' antibodies. Briefly, Nunc Maxisorp ELISA plates were passively coated with 100 ng/well of recombinant human Hsp70B', recombinant human Hsp70A (SPP-755, Stressgen Biotechnologies), recombinant bovine Hsc70 (SPP-751, Stressgen Biotechnologies), recombinant hamster Grp78 (SPP-765, Stressgen Biotechnologies), E. coli DnaK (SPP-630, Stressgen Biotechnologies) and recombinant M. tuberculosis Hsp71 (Stressgen Biotechnologies) diluted in PBS. Similarly, unconjugated CB2, ECB, TCB, and CE peptides were diluted in PBS and coated at 0.5 μg/well. Plates were blocked with 200 l/well of casein blocking buffer in PBS (Pierce) for 2 hours at room temperature. Test and negative control antibodies were diluted to a starting concentration/dilution of 1 μg/ml for affinity purified antibodies and 1:1000 for serum antibodies in Stabilzyme Select (SurModics). Diluted antibodies were added to the plate wells and were further diluted by 5 serial titrations at a ratio of 1:3 to a final concentration/dilution of 4.1 ng/ml (for purified antibodies) and 1:243000 (for serum antibodies). Plates were incubated for 1 hour at room temperature with diluted primary antibody, followed by another 1 hour room temperature incubation with peroxidase conjugated anti-rabbit IgG (SAB-300, Stressgen Biotechnologies), diluted 1:25000 in Stabilzyme Select. Plates were developed with TMB (BioFx) for 5–10 minutes at room temperature and the reaction was stopped with acid stop solution (BioFx). Absorbance of each well was measured at 450 nm in an EL808 microplate reader (BioTek), interfaced with KC3 software. The titre of the antibody was represented as the concentration or reciprocal dilution of the antibody that resulted in an absorbance reading of 0.2.

A relative titre index was established to compare the titre of the test antibody against a negative control antibody. For affinity purified antibodies, the index value was calculated by dividing the titre of the negative control antibody by the titre of the test antibody. For serum antibodies, the index value was calculated by dividing the titre of the test antibody by the titre of the negative control antibody.

Competition EIA. Nunc Maxisorp ELISA plates (primary plates) were passively coated overnight at 4° C. with 100 ng/well of purified recombinant human Hsp70B' diluted in PBS. After washing six times with PBS containing 0.05% tween-20, primary plates were incubated with 200 μl/well of Superblock blocking buffer in PBS (Pierce) at room temperature.

While the primary plates were blocking, the free antigen:antibody mixtures were prepared in 96 well Nunc polypropylene plates (secondary plates). First, Hsp70B' standard and Hsp70 protein homologs (i.e. cross reactants; recombinant human Hsp70A, recombinant bovine Hsc70, recombinant hamster Grp78, E. coli DnaK, and M. tuberculosis Hsp71) were diluted to a starting concentration of 10 μg/ml and 500 μg/ml respectively in BSA diluent (0.12% BSA (Sigma), 0.05% tween-20 (BioRad), 1:1000 ProClin 200 (Supelco) in PBS). The diluted proteins were added to the secondary plates and then serially titrated four times at a ratio of 1:5 in BSA diluent to generate a Hsp70B' concentration range of 0.016–10 μg/ml and a homolog concentration range of 0.8–500 μg/ml in a final volume of 100 μl/well. BSA diluent alone served as the 0 μg/ml point.

The rabbit CB2 affinity purified antibody, CE and 70B' WP serum antibodies were diluted to 0.06 μg/ml, 1:10,000 and 1:16,000 respectively in BSA diluent. An equal volume (100 μl/well) of diluted antibody was added to the secondary plate wells with BSA diluent and varying concentrations of Hsp70B' and homolog. The secondary plate was incubated at room temperature for 1.75 hours, after which 100 μl of the free antigen:antibody mixture was transferred to the blocked and washed primary plates. Primary plates were incubated at room temperature for 1 hour at room temperature, followed by a 1 hour room temperature incubation with peroxidase conjugated anti-rabbit IgG secondary antibody (SAB-300, Stressgen Biotechnologies) diluted in BSA diluent. The primary plate was developed with TMB (BioFx) and stopped with acid stop solution (BioFx) after 10 minutes. The absorbance of each well was read with a BioTek EL808 microplate reader set at 450 nm. The maximum absorbance (i.e. $A_{max}$; maximum amount of antibody binding at 0 μg/ml free Hsp70B' or homolog) was determined and used to calculate the % $A/A_{max}$ at each Hsp70B' or homolog competition concentration. Antibody displacement curves were generated by plotting the % $A/A_{max}$ against the concentration of free Hsp70B' or homolog.

Cloning and Expression of Recombinant Human Hsp70B'. Human Hsp70B' was cloned from heat shocked HeLa cells and expressed recombinantly in E. coli. Briefly, $2 \times 10^7$ HeLa cells were heat shocked for 2 hours at 44° C. and then immediately harvested. Poly (A+) RNA was isolated from the heat shocked HeLa cells with a mRNA isolation kit (Boehringer Mannheim) and used to synthesize human Hsp70B' cDNA by RT-PCR. The 51 μl RT-PCR reaction mixture consisted of 1 μl of 10 mM dNTP (Perkin Elmer), 2.5 μl of 100 mM DTT (Boehringer Mannheim), 0.25 μl of 40 units/μl RNase inhibitor (Boehringer Mannheim), 10 μl of 5×RT-PCR buffer containing 7.5 mM $MgCl_2$ and DMSO (Boehringer Mannheim), 1 μl of enzyme mix (Boehringer Mannheim) containing Expand High Fidelity enzyme mix and AMV reverse transcriptase, 0.87 μg of poly (A+) RNA from heat shocked HeLa cells, and 1 μg each of: primer 1: 5'-GAAGCTTCACATATGCAGG CCCCACGGGAGCTCG-3' (SEQ ID NO:12) and primer 2: 5'-GAAGCTCGAGTCAATCAACCTCCTCAATGA-3' (SEQ ID NO:13).

The primer sequences were derived from the human Hsp70B' nucleotide sequence (Leung et al., 1990) and designed to introduce a NdeI restriction site upstream of the start codon and a XhoI restriction site downstream of the stop codon. The cDNA was synthesized by incubating the reaction mixture for 30 minutes at 50° C. and amplified by PCR in a Perkin Elmer Gene Amp PCR System 2400 which was programmed for 2 minutes at 94° C., followed by 10 cycles of 30 seconds at 94° C., 30 seconds at 60° C., 2 minutes at 68° C., and 15 cycles of 30 seconds at 94° C., 30 seconds at 60° C., and 2.5 minutes at 68° C.; the last extension step was 7 minutes at 68° C. The reaction product was analyzed by agarose gel electrophoresis and ethidium bromide staining. The human Hsp70B' cDNA was digested with NdeI (New England BioLabs) and XhoI (New England BioLabs) and ligated into a similarly digested pET24a (Novagen) expression vector. The resulting expression plasmid carrying human Hsp70B' was transformed into E. coli BLR (DE3) and BL21 (DE3) cells. For preparation of bacterial extracts, cells were grown at 37° C. in LB medium (Difco) containing 30 μg/ml kanamycin (Sigma). When the cells reached an $OD_{595}$ of 0.5, 1 mM isopropyl β-D-thiogalactopyranoside (Amersham) was added to the medium and the culture was incubated at 37° C. for an additional 2.5 hours. Cell pellets were resuspended with lysis buffer (50 mM Tris pH 7.5 (BDH), 150 mM NaCl (BDH), 0.1 mM phenylmethylsulfonyl fluoride (Sigma), 1 μg/ml leupeptin (Sigma) and 1 μg/ml aprotinin (Sigma)) and disrupted by sonication. The Bradford assay (Bio-Rad) was used to determine the protein concentration of the extract. The extract was diluted in SDS-PAGE sample buffer (40 mM Tris-HCl pH 6.8 (BDH), 1% SDS (Bio-Rad), 50 mM DTT (ICN), 7.5% glycerol [Anachemia], and 0.003% bromophenol blue (Sigma)) and boiled for 5 minutes in preparation for SDS-PAGE and immunoblotting.

Cloning and Expression of Recombinant $His_6$-Human Hsp70B (Fragment). The 741 bp fragment that encodes a portion of the amino terminus region of the human Hsp70B was obtained from SPD-925, a human Hsp70B stress gene probe (Stressgen Biotechnologies). SPD-925 is supplied as a plasmid containing 3.15 kb of the 5' non-transcribed Hsp70B gene sequence, the 119 bp RNA leader region and the 741 bp protein coding region. Although the protein coding region can be excised from SPD-925 by digestion with HindIII, restriction site modifications were introduced by PCR. The 50 µl PCR reaction mixture consisted of 8 µl of 1.25 mM dNTP (New England BioLabs), 5 µl of 10×Expand High Fidelity PCR buffer (Boehringer Mannheim), 0.5 µl of 3.5 units/µl Expand High Fidelity DNA polymerase (Boehringer Mannheim), 0.05 µg of SPD-925, and 1 µg each of primer 1:

5'-GAAGCTTCACATATGCAGGCCCCACGGGA GCTCG-3'(SEQ ID NO:12) and primer 2 5'-TGACAAGCTTAGAATTCTTCCATGAAGTGGT-3' (SEQ ID NO:14).

The primer sequences were derived from the human Hsp70B nucleotide sequence (Voellmy et al., 1985). Primer 1 was designed to introduce an NdeI restriction site upstream of the start codon whereas primer 2 was designed to introduce a stop codon and a HindIII restriction site. The PCR reaction was performed in a Perkin Elmer Gene Amp PCR System 2400 which was programmed for 2 minutes at 94° C., followed by 10 cycles of 30 seconds at 94° C., 30 seconds at 60° C., 1 minute at 72° C., and 15 cycles of 30 seconds at 94° C., 30 seconds at 60° C., and 1.25 minutes at 72° C.; the last extension step was 7 minutes at 72° C. The reaction product was analyzed by agarose gel electrophoresis and ethidium bromide staining. The human Hsp70B PCR product was digested with NdeI (New England BioLabs) and HindIII (New England BioLabs) and ligated into a similarly digested pET28a (Novagen) expression vector. The resulting expression plasmid carrying $his_6$-human Hsp70B was transformed into E. coli BLR (DE3) cells. For preparation of bacterial extracts, cells were grown at 37° C. in LB medium (Difco) containing 30 µg/ml kanamycin (Sigma). When the cells reached an $OD_{595}$ of 0.5, 1 mM isopropyl β-D-thiogalactopyranoside (Amersham) was added to the medium and the culture was incubated at 37° C. for an additional 2.5 hours. Cell pellets were resuspended with SDS-PAGE sample buffer, sonicated, and boiled for 5 minutes in preparation for SDS-PAGE and immunoblotting.

Purification of Recombinant Human Hsp70B' Protein. E coli BL21 (DE3) cells harboring the expression plasmid for full length human Hsp70B' were grown in LB media with 30 µg/ml kanamycin (Sigma) at 37° C. with shaking at 250 rpm. At an $OD_{595\ nm}$ of 0.5–0.6, expression of recombinant protein was induced with 1 mM isopropyl β-D-thiogalactopyranoside (IPTG; Calbiochem) and cells were harvested by centrifugation after 3 hours. Bacterial pellets were resuspended with lysis buffer (25 mM Tris-HCl pH 7.5 (BDH), 5 mM EDTA (Sigma), 0.3 mg/ml lysozyme (Sigma), 5 mM p-aminobenzamidine (Sigma), 15 mM β-mercaptoethanol (BME; Sigma), 1 mM phenylmethylsulfonyl fluoride (PMSF; Sigma), 1 µg/ml aprotinin (Sigma), 1 µg/ml leupeptin (Sigma)) and disrupted by sonication. The bacterial suspension was centrifuged and the supernatant was loaded onto a Q sepharose (Amersham Pharmacia) ion exchange column. Bound protein was eluted with a 0–300 mM NaCl gradient, followed by a 300 mM NaCl wash. Q-Sepharose fractions were analyzed on coomassie stained SDS-PAGE gels and the Hsp70B' containing fractions pooled. $MgCl_2$ (Sigma) was added to a final concentration of 3 mM and the pool was loaded onto an ATP agarose (Flulca) column. After 500 mM NaCl and 20 mM NaCl washes, bound Hsp70B' protein was eluted with ATP agar elution buffer (10 mM Tris-HCl pH 7.5, 3 mM $MgCl_2$, 10 mM ATP (Sigma), 15 mM BME, 0.1 mM PMSF, 1 µg/ml aprotinin, 1 µg/ml leupeptin). Hsp70B' containing fractions were pooled and sodium acetate (Mallinckrodt) pH 5.5 added to a final concentration of 40 mM. The pool was adjusted to pH 5.5 with acetic acid (Fisher Scientific) and then loaded onto a SP HiTrap (Amersham Pharmacia) ion exchange column. Protein was eluted with a 0–1M NaCl gradient. Hsp70B' containing fractions were pooled and the protein preparation was dialyzed and stored in 10 mM Tris-HCl pH 7.5, 150 mM NaCl buffer. Protein concentration was determined by the Bradford assay (Bio-Rad) and purity was assessed by densitometry scanning of a coomassie stained SDS gel with 0.5, 1.0 and 1.5 µg Hsp70B'.

Cell Culture was performed as follows. HeLa (human epitheloid cervical carcinoma, ATCC CCL-2) cells were grown in Eagle's minimal essential medium with Earle salts (ICN) supplemented with 0.1 mM non-essential amino acids (Gibco), 2 mM L-glutamine (Gibco), 10% fetal bovine serum (Gibco), 50 µg/ml gentamycin sulfate (Gibco), and 1 mM sodium pyruvate (Gibco). Jurkat (clone E6-1, human acute T-cell leukemia, ATCC TIB-152) cells were grown in RPMI 1640 medium (Gibco) supplemented with 10% fetal bovine serum (Gibco), 2 mM L-glutamine (Gibco), 1.5 g/L sodium bicarbonate (ICN), 10 mM HEPES (Gibco), 4.5 g/L glucose (Sigma), 1 mM sodium pyruvate (Gibco), and 50 µg/ml gentamycin sulfate (Gibco), and 1.5 g/L sodium bicarbonate (ICN). Vero (African green monkey, normal kidney epithelial, ATCC CCL-81) cells were grown in Eagle's minimal essential medium with Earle salts (ICN) supplemented with 2 mM L-glutamine (Gibco), 0.1 mM non-essential amino acids (Gibco), 1 mM sodium pyruvate (Gibco), 0.1 mM non-essential amino acids, 50 µg/ml gentamycin sulfate (Gibco) and 10% fetal bovine serum (Gibco). CHO-K1 (Chinese hamster ovary epithelial, ATCC CCL-61) cells were grown in Dulbecco's modified Eagle's medium (Gibco) supplemented with 2 mM L-glutamine, 10 mM HEPES (Gibco), 50 µg/ml gentamycin sulfate (Gibco) and 5% fetal bovine serum (Gibco). MDBK (bovine normal kidney epithelial, ATCC CCL-22) cells were grown in Eagle's minimal essential medium with Earle salts (ICN) supplemented with 2 mM L-glutamine (Gibco), 0.1 mM non-essential amino acids (Gibco), 1 mM sodium pyruvate (Gibco), 50 µg/ml gentamycin sulfate (Gibco) and 10% horse serum (Gibco). HeLa, Jurkat, Vero, CHO and MDBK cells were incubated at 37° C. in a water-jacketed incubator with 5% $CO_2$. A-431 cells were similarly incubated at 37° C., but with 10% $CO_2$.

Treatment with Metals, Azetidine and Heat. At 90% confluency, HeLa, A-431 and Jurkat cells were incubated at 37° C. for 2 hours with 100 µM $CdCl_2$ (Sigma) or 250 µM $ZnCl_2$ (Sigma) and harvested after a 5 hour recovery period in media without $CdCl_2$ or $ZnCl_2$. Cells were similarly treated for 5 hours with 5 mM of the proline analogue, L-azetidine-2-carboxylic acid (Sigma), and harvested after a 2 hour recovery period. Cells were also heat shocked for 20 minutes or 2 hours at 44° C. and harvested after a 5 hour recovery period at 37° C. Cell lysates were prepared for SDS polyacrylamide gel electrophoresis and immunoblot analysis.

Vero, CHO and MDBK cells were also subjected to heat stress. Vero cells were heat stressed for 1.5 hours at 42° C. and recovered at 37° C. for 18 hours prior to harvesting. CHO cells were heat stressed for 2 hours at 42° C. and recovered at 37° C. for 18 hours prior to harvesting. MDBK cells were heat stressed for 1.5 hours at 44° C. and harvested after an 18 hour recovery at 37° C. Cell lysates were prepared for SDS polyacrylamide gel electrophoresis and immunoblot analysis.

Heat Treatment of HeLa Cells. HeLa cells were grown to 90% confluency and heated for 2 hours at 37° C., 38.5° C., 40° C., 41.5° C., 43° C., and 44.5° C. Cells were harvested after a 5 hour recovery period at 37° C. and prepared for SDS polyacrylamide gel electrophoresis and immunoblot analysis.

Recovery of Heat Treated HeLa Cells. HeLa cells were grown to 90% confluency and heated for 2 hours at 44.5° C. Cells were harvested after recovering at 37° C. for 0, 2.5, 5, 16 and 24 hours. Control cells were maintained at 37° C. and were similarly harvested at the same recovery times. Cell lysates were prepared for SDS polyacrylamide gel electrophoresis and immunoblot analysis.

SDS Polyacrylamide Gel Electrophoresis and Immunoblotting. After the appropriate recovery period, cells were washed with Dulbecco's phosphate buffered saline without calcium and magnesium (ICN) and harvested with a cell scraper. Harvested cells were resuspended with lysis buffer (Dulbecco's phosphate buffered saline without calcium and magnesium (ICN), 0.05% triton-X100 (Sigma), 0.1 mM phenylmethylsulfonyl fluoride (Sigma), 1 µg/ml leupeptin (Sigma) and 1 µg/ml aprotinin (Sigma)) and disrupted by sonication. The protein content of the cellular extracts was determined by the Bradford method (Bio-Rad). The extract was diluted in SDS buffer containing 40 mM Tris-HCl pH 6.8 (BDH), 1% SDS (Bio-Rad), 50 mM DTT (ICN), 7.5% glycerol (Anachemia), and 0.003% bromophenol blue (Sigma) and heated at 70° C. for 5 minutes. Cell extracts were resolved on 12.5% SDS polyacrylamide gels and separated proteins were electroblotted onto nitrocellulose membranes (Gelman Sciences) by using a 25 mM Tris (BDH), 192 mM glycine (Fisher Scientific), 20% (v/v) methanol (Fisher Scientific) transfer buffer in a Trans-Blot apparatus (Bio-Rad) at 100 V for 1 hour. Blots were blocked in 5% Carnation non-fat milk, 0.05% Tween-20 (Bio-Rad), 0.02% $NaN_3$ (Fisher Scientific) or thimerosal (Fisher Scientific) in phosphate buffered saline (15.4 mM $Na_2HPO_4$ (Mallinckrodt), 4.6 mM $NaH_2PO_4$ (Mallinckrodt), 120 mM NaCl (BDH)). Blots were probed with a mouse monoclonal antibody specific for inducible Hsp70A and Hsp70B' (Stressgen Biotechnologies, SPA-810), rabbit polyclonal antibody specific for inducible Hsp70A (Stressgen Biotechnologies, SPA-812), rat monoclonal antibody specific for cognate Hsc70 (Stressgen Biotechnologies, SPA-815), rabbit polyclonal antibody for Hsp110 (Stressgen Biotechnologies, SPA-1101), mouse monoclonal antibody specific for Grp75 (Stressgen Biotechnologies, SPA-825), mouse monoclonal antibody specific for the endoplasmic reticulum KDEL retention signal peptide (Stressgen Biotechnologies, SPA-827), mouse monoclonal antibody specific for E. coli DnaK (Stressgen Biotechnologies, SPA-880), mouse monoclonal antibody specific for M. tuberculosis Hsp71 (Stressgen Biotechnologies, SPA-885), and polyclonal antibodies raised either against a panel of synthetic peptides derived from the linear human Hsp70B' sequence or purified recombinant human Hsp70B'. Blots were incubated for 1 hour at room temperature with primary antibodies diluted in blocking buffer. Alkaline phosphatase or peroxidase conjugated secondary antibodies (Stressgen Biotechnologies) were respectively diluted 1:1000 and 1:5000 in blocking buffer and incubated with the blots for 1 hour at room temperature. Blots using alkaline phosphatase conjugated secondary antibodies were developed with 0.15 mg/ml 5-bromo-4-chloro-3-indolyl phosphate (Sigma) and 0.3 mg/ml nitro blue tetrazolium (Sigma) in alkaline phosphatase buffer (100 mM Tris-HCl pH 9.5 (BDH), 150 mM NaCl (BDH), 10 mM $MgCl_2$ (Fisher Scientific)). The developed blots were washed with deionized water to stop the colour reaction. Blots using peroxidase conjugated secondary antibodies were developed by enhanced chemiluminescence (ECL, Amersham).

Generation of Mouse Hybridomas. BALB/c mice were immunized with Hsp70B' peptide-KLH conjugate essentially as already described. Test bleeds were analyzed for anti-peptide and anti-Hsp70B' protein serum titres by indirect EIA and mice with high Hsp70B' titres were selected for fusion. Four days prior to splenectomy and cell fusion, the selected mice were boosted with antigen in the absence of adjuvant. Mouse spleens were aseptically removed, minced with forceps and strained through a sieve. Cells were washed twice with IMDM medium and counted using a hemocytometer. Spleen cells were mixed with mouse myeloma P3×63Ag8.653 cells at a ratio of 5:1 (spleen:myeloma cells) and centrifuged. Cell pellets were resuspended with 1 ml of 50% PEG (MW 1450), added dropwise over a period of 30 seconds. The resuspended cells were gently mixed for 30 seconds using a pipette and then allowed to stand undisturbed for another 30 seconds. 5 ml of IMDM media was added over a period of 90 seconds, followed immediately with another 5 ml. The resulting cell suspension was left undisturbed for 5 minutes, after which the cells were pelleted and resuspended at $5\times10^5$ cells/ml in HAT medium (IMDM containing 10% FBS, 2 mM L-glutamine, 0.6% 2-mercaptoethanol, hypoxanthine, aminopterin, thymidine, and 10% Origen growth factor). Cells were plated into 96 well plates at $10^5$ cells/well. Plates were incubated at 37° C. in a 7% $CO_2$ atmosphere with 100% humidity. Seven days after fusion, the media was removed and replaced with IMDM containing 10% FBS, 2 mM L-glutamine, 0.6% 2-mercaptoethanol, hypoxanthine and thymidine. 10–14 days after fusion, the supernatant was taken from wells with growing hybridoma colonies and screened for anti-peptide and anti-protein antibody by indirect EIA. Hybridoma cells from positive wells were cloned by limiting dilution in 96 well plates at a density of 0.25 cells per well or one cell in every fourth well. Growing colonies were tested 10–14 days later using the same assay(s) used to initially select the hybridomas. Positive clones were expanded and frozen.

RESULTS

Eight peptide sequences were chosen, one an N-terminus epitope as well as seven epitopes from the carboxyl end of the human Hsp70B' protein. Peptide sequences were selected based on minimal identity and homology with other HSP70 family members and algorithmic predictions of hydrophilicity (Kyte-Doolittle), antigenicity (Jameson-Wolf) and surface probability (Emini). These sequences, their respective residue numbers (according to the GeneBank sequence #P 17066) and epitope designations are listed in Table 1. The CB and CB2 sequences are the same, except the CB2 peptide was synthesized on a separate occasion.

TABLE 1

Summary of Immunogenicity of Different Hsp70B' Epitopes

| Epitope (Ab) Name | Location (P17066) | Peptide Immunogen | Animal Host | Antisera Titer (EIA) | # Animals Responding |
|---|---|---|---|---|---|
| *CB | 624–638 | KLH-CGTQARQGDPSTGPI | Rabbit | >204,800<br>33,021<br>>204800 | 3/3 |
| *CA | 561–573 | KLH-(C)RDKIPEEDRRKMQ | Rabbit | >204,000<br>>204,800<br>191,311 | 3/3 |
| *CD | 561–576 | RDKIPEEDRRKMQDKC-KLH | Rabbit | >204,000<br>>204,800 | 2/2 |
| *CC | 546–559 | KLH-AHVFHVKGSLQEES | Rabbit | >204,000<br>>204,800<br>>204,800 | 3/3 |
| *NT | 1–12 | MQAPRELAVGID(C)-KLH | Rabbit | >204,000<br>168,019<br>>204,800 | 3/3 |
| ECB | 618–638 | KLH-vpggsscgtqarqgdpstgpi | Rabbit | >204800<br>>204800<br>>204800 | 3/3 |
| TCB | 624–635 | KLH-CGTQARQGDPST | Rabbit | >204800<br>>204800<br>>204800 | 3/3 |
| CE | 553–567 | KLH-GSLQEESLRDKIPEE | Rabbit | 8424<br>67510<br>4368 | 3/3 |
| *CB2 | 624–638 | KLH-CGTQARQGDPSTGPI | Rabbit | >204800<br>>204800<br>>204800 | 3/3 |
| CB2 | 624–638 | KLH-CGTQARQGDPSTGPI | Goat | 4200 | 1/1 |
| CB2 | 624–638 | KLH-CGTQARQGDPSTGPI | Mouse | >204800<br>111432<br>>204800<br>>208400<br>36685<br>108253<br>151239<br>>204800<br>64358<br>>204800 | 10/10 |
| 70B' WP | Hsp70B' 1–643 | full length recombinant human Hsp70B' protein | Rabbit | >243000<br>123100<br>222900 | 3/3 |

*indicates antisera subsequently purified by peptide immunoaffinity chromatography.

The peptides were synthesized, conjugated to KLH and used to immunize rabbits, goats or mice. Specific antibody responses to the immunizing peptide were detected in every animal as assessed by indirect peptide EIA (Table 1). Six of the nine rabbit anti-peptide antisera were then purified by peptide immunoaffinity chromatography. Antibody preparations were tested for specificity of binding with a panel of HSP70 protein homologs as well as a series of stressed and non-stressed human and mammalian cell lysates (Tables 2–6).

Hsp70B'Antibody Production with Recombinant Human Hsp70B' Protein.

In addition to generating Hsp70B' antibodies via the peptide immunization route, a Hsp70B' antibody, designated 70B' WP, was produced in rabbits using purified (i.e. ~90% homogeneity) recombinant human Hsp70B' as the immunogen. Like the peptide generated antibodies, the antibody response to the immunizing protein was detected in each rabbit by indirect ETA (Table 1). The sera was pooled and then tested for specificity against a panel of purified HSP70 homologs by indirect EIA (Table 2) and competition EIA. (Table 3) The antisera was also assessed by immunoblotting with control and heat stressed cell lysates (Tables 5 and 6).

Determination of Antibody Specificity by Relative Titre Index

The specificity of selected Hsp70B' antibodies was determined by indirect ETA and expressed as an antibody titre index, relative to an irrelevant or negative control antibody (Table 2). Titre is defined as the antibody concentration (for purified antibodies) or reciprocal dilution (for unpurified antisera) that results in 0.2 absorbance units. This cutoff value approximately represents the absorbance of the assay background+3 standard deviations. It is the lowest distinguishable positive signal at 95% confidence.

The relative titre index directly compares the titres of the Hsp70B' antibodies with the titre of an irrelevant antibody. It is therefore a measurement of antibody reactivity towards a particular protein or peptide above non-specific binding. The index value is directly proportional to the reactivity of the antibody. Thus, the higher the relative index, the more reactive the antibody is toward a particular protein or peptide. An index of 1 reflects reactivity that is on par with that of the negative control antibody and is considered as negligible binding. An index value greater than 1 is indicative of binding. If an antibody is found to react with only one protein or peptide (e.g. the antibody has an index of >1 with only one protein or peptide), specificity can be defined within the context of the proteins or peptides tested.

Based on absolute index values in Table 2, the CB2, CE, ECB and TCB antibodies preferentially reacted with Hsp70B' by 177, 48, 41 and 29 fold respectively over other HSP70 protein homologs. Under these assay conditions, the CB2, CE, ECB and TCB antibodies were specific for Hsp70B' protein.

At lower dilutions, the 70B' WP antibody minimally exhibited some cross reactivity with Hsp70A, DnaK, and likely with Hsc70 and Hsp71. However, the 70B' WP antibody still reacted 90 fold higher with Hsp70B' over Hsp70A and DnaK. SPA-812 is a rabbit polyclonal antibody produced to recombinant human Hsp70A protein. In addition to reacting with Hsp70A, SPA-812 also cross reacted with Hsp70B' (and likely with Hsc70 and DnaK) at lower dilutions. For both of these whole protein antibodies, reactivity with their respective antigens was high (index>100). Therefore, by using the antibodies at higher dilutions, cross reactivity can likely be "diluted out" and reactivity to the intended protein still retained. This essentially selects for the population of higher affinity antibodies that recognize specific epitopes on the antigen of interest.

The 70B' WP antibody reacted 4–6 fold higher with Hsp70B' protein over the CE, ECB and TCB serum antibodies. However, the 70B' WP antibody also exhibited cross reactivity with other homologs whereas the peptide antibodies did not. This is not unexpected since the 70B' WP antibody likely consists of several antibody populations that recognize different Hsp70B' epitopes throughout the surface of the molecule. Some of these epitopes though are likely shared or homologous epitopes with other homologs. The peptide antibodies probably also consist of several antibody populations that recognize Hsp70B', but the epitopes are limited to the immunizing peptide sequence, thus limiting cross reactivity. This supports the peptide approach over whole protein immunizations, if specific Hsp70B' polyclonal antibodies are required. Reactivity of peptide polyclonal antibodies with the intended protein can also be enhanced by affinity purification, as illustrated by the purified CB2 antibody. Under these assay conditions, this antibody had a high index value (i.e. >100) for Hsp70B' and was specific for Hsp70B'. Of course, the 70B' WP could also be affinity purified to enhance specificity, thus increasing the usefulness of this antibody if required at lower dilutions.

The CB2 and ECB antibodies reacted with the reciprocal immunizing peptide. This was not unexpected since ECB was just an extension of CB2. Similarly, the CB2 and ECB antibodies were expected to react with the TCB peptide, the truncated version of CB2. However, the CB2 antibody did not react with the TCB peptide and the ECB antibody had some reactivity to the TCB peptide that was beyond the lower limits of the assay. 70B' WP also did not react with the TCB peptide, but there was some reactivity with the CB2, ECB and CE peptides. This suggests that more antigenic epitopes on the Hsp70B' protein are responsible for the reactivity of 70B'WP. The TCB antibody reacted with the immunizing peptide and both the CB2 and ECB peptides.

TABLE 2

Relative Titre Index of Hsp70B' Antibodies

| | Purified Antibodies | | Rabbit Antibody Serum Antibodies | | | | | |
|---|---|---|---|---|---|---|---|---|
| Hsp Protein or Hsp70B' Peptide | CB2 Hsp70B' 624–638 | NSF NSF 721–744 | CE Hsp70B' 553–567 | ECB Hsp70B' 618–638 | TCB Hsp70B' 624–635 | 70B' WP Hsp70B' 1–643 | SPA812 Hsp70A 1–641 | Normal Rabbit Serum |
| Hsp70B' Protein | ≧177 | 1 | ≧48 | ≧41 | ≧29 | ≧182 | ≧12 | 1 |
| Hsc70 Protein | 1 | 1 | 1 | 1 | 1 | *1 | *1 | 1 |
| Hsp70A Protein | 1 | 1 | 1 | 1 | 1 | ≧2 | ≧143 | 1 |
| DnaK Protein | 1 | 1 | 1 | 1 | 1 | ≧2 | *1 | 1 |
| Grp78 Protein | 1 | 1 | 1 | 1 | 1 | 1 | 1 | 1 |
| Hsp71 Protein | 1 | 1 | 1 | 1 | 1 | *1 | 1 | 1 |
| CB2 Peptide | ≧92 | 1 | 1 | ≧86 | ≧37 | ≧5 | 1 | 1 |
| ECB Peptide | ≧209 | 1 | 1 | ≧129 | ≧57 | ≧9 | 1 | 1 |
| TCB Peptide | 1 | 1 | 1 | *1 | ≧243 | 1 | 1 | 1 |
| CE Peptide | 1 | 1 | ≧201 | 1 | 1 | ≧7 | 1 | 1 |

Irrelevant antibodies used to assess non-specific binding are shaded in gray. For purified antibodies, index values were calculated by dividing the titre of the irrelevant antibody by the titre of the test antibody. For serum antibodies, the index values were calculated by dividing the titre of the test antibody by the titre of the irrelevant antibody.

Determination of Antibody Specificity by Competition EIA

Selected Hsp70B' antibodies were evaluated in a competition EIA as another method for assessing antibody specificity. This competition EIA was based on the 50% displacement method for calculating cross reactivity (Abraham, G. E., *J. Clin. Endocrinol. Metab.* 29:866–870, 1969). As described by Abraham, a constant amount of antibody and labeled standard (S) are incubated in the presence of varying doses of unlabeled S or cross reactant (CR). The unlabeled S or CR is the "displacer" that competes with the labeled S for antibody binding sites. The bound labeled S is then quantified at each dose of unlabeled S or CR. Displacement curves are generated by plotting the % $B/B_0$ against the dose of unlabeled S or CR. B is the amount of bound labeled S in the presence of added unlabeled S and $B_0$ is the amount of bound labeled S in the absence of added unlabeled S (i.e. maximum bound labeled standard). In the 50% displacement method, cross reactivity is the ratio of unlabeled S to CR doses that give 50% displacement of bound labeled S, expressed as a percentage.

A competition EIA was developed to determine the specificity of selected Hsp70B' antibodies. Labeled standard is required for the competition reaction described by Abraham. However, labeled Hsp70B' protein was unavailable for this study. Instead, the competition reaction was modified to measure the amount of antibody binding to a constant amount of S bound to a solid phase, in the presence of varying amounts of free S or CR. Displacement curves were generated by plotting the %A/Amax against the dose of the free displacer, where A was the amount of antibody bound in the presence of displacer and Amax was the amount of antibody bound in the absence of displacer. Similar to the Abraham method, cross reactivity was defined as the ratio of the free standard and cross reactant doses that resulted in 50% displacement (A/Amax) of bound antibody.

Figure 1B:
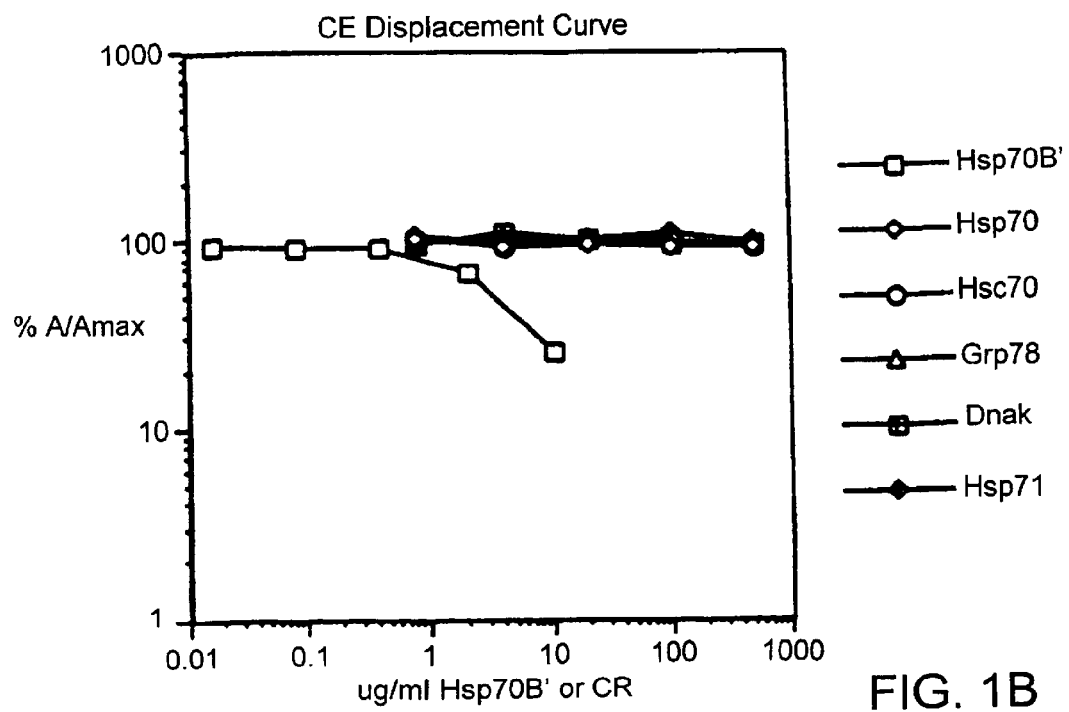
Figure 1C:
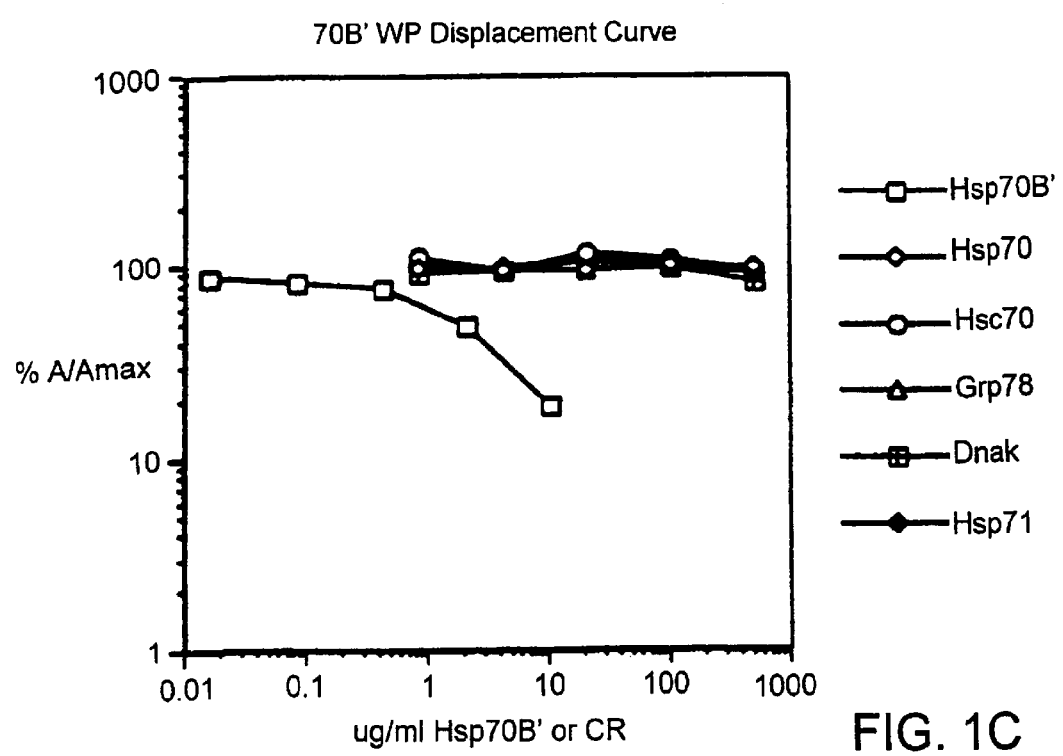

Displacement curves for CB2 (FIG. 1A, purified rabbit antibody), CE (FIG. 1B) and 70B' WP (FIG. 1C) antibodies were generated with Hsp70B' protein (S) and five HSP70 homologs (CR): Hsp70A, Hsc70, Grp78, DnaK and Hsp71. The concentration range of the free Hsp70B' protein was 0.016–10 µg/ml whereas the range for the cross reactants was 0.8–500 µg/ml. For all three Hsp70B' antibodies, there was no distinct competition from the cross reactants when compared to Hsp70B', despite using 50 fold more cross reactant at the highest dose. Under these assay conditions, a 50% displacement concentration could not be obtained for the cross reactants since the average % A/Amax values throughout the cross reactant concentrations ranged from 93–100%. It was unsuitable to redefine the 50% displacement cutoff to 5% (i.e. % A/Amax of 95%) since variability of the assay could account for that level of displacement, rather than being a true competition. In any case, higher cross reactant concentrations beyond 500 µg/ml are required for a more accurate assessment.

In Table 3, the percentage of cross reactivity with HSP70 homologs are presented for the CB2, CE and 70B' WP antibodies. Since the 50% displacement doses for the cross reactants were unobtainable, >500 µg/ml was reported and 500 µg/ml was used for calculating the cross reactivity. The cross reactivity percentages are therefore actually lower than the absolute reported values. Based on this data and under these assay conditions, the CB2, CE and 70B' WP antibodies were more reactive with Hsp70B' by at least 758, 142 and 263 fold respectively over the tested HSP70 homologs. The CB2 antibody is notably more reactive with Hsp70B' than the CE and 70B' WP antibodies. This is likely because the CB2 antibody was affinity purified, whereas CE and 70B' WP were antisera. The CB2 antibody was competed with lower amounts of free standard, suggesting that this preparation contained a greater proportion of higher affinity antibodies as compared to the CE and 70B' WP antibodies.

The CB2 and CE antibodies were considered specific for Hsp70B' when expressed in terms of a relative titre index (Table 2). Under the competition EIA conditions, these two antibodies can also be considered specific for Hsp70B'. The 70B' WP antibody, however, was not specific for Hsp70B' at lower dilutions (e.g. 1:2000) by relative titre index. The competition assay used 70B' WP at a dilution that was 16 fold higher. This indicates that cross reactivity can essentially be "diluted out" for this antibody and perhaps should be used at higher dilutions to maximize specificity.

Displacement Curves for rabbit Hsp70B' antibodies: CB2 (A), CE (B) and 70B' WP (C). HSP70 homologs were unable to significantly displace CB2, CE and 70B' WP antibody binding to solid phase Hsp70B'. Under these assay conditions, CB2, CE and 70B' WP are specific for Hsp70B'.

TABLE 3

Specificity of Selected Hsp70B' Antibodies in terms of Cross Reactivity with Hsp70 Homologs

| Rabbit Hsp70B' Antibody | Free Displacer (Standard or Cross Reactant) | Concentration of Free Displacer at 50% A/Amax (µg/ml) | % Cross Reactivity |
|---|---|---|---|
| CB2 (Purified) | Hsp70B' (S) | 0.66 | 100% |
| | Hsp70 (CR) | >500 | <0.13% |
| | Hsc70 (CR) | >500 | <0.13% |
| | Grp78 (CR) | >500 | <0.13% |
| | DnaK (CR) | >500 | <0.13% |
| | Hsp71 (CR) | >500 | <0.13% |
| CE (Antisera) | Hsp70B' (S) | 3.52 | 100% |
| | Hsp70 (CR) | >500 | <0.70% |
| | Hsc70 (CR) | >500 | <0.70% |
| | Grp78 (CR) | >500 | <0.70% |
| | DnaK (CR) | >500 | <0.70% |
| | Hsp71 (CR) | >500 | <0.70% |
| 70B' WP (Antisera) | Hsp70B' (S) | 1.88 | 100% |
| | Hsp70 (CR) | >500 | <0.38% |
| | Hsc70 (CR) | >500 | <0.38% |
| | Grp78 (CR) | >500 | <0.38% |
| | DnaK (CR) | >500 | <0.38% |
| | Hsp71 (CR) | >500 | <0.38% |

Cross reactivity was calculated by dividing the concentration of free standard by the concentration of cross reactant at 50% A/Amax. The ratio was then expressed as a percentage.

Determination of Antibody Specificity by Immunoblotting

Each of the Hsp70B' antibodies detected their respective epitopes in the synthetic peptide, the peptide-KLH conjugate, the recombinant Hsp70B' protein as well as in the native Hsp70B' protein present in cultured cell lysates. Antibody binding to native Hsp70B' protein in cell lysates was determined by immunoblotting. Several control antibodies were included in these experiments to validate the assays and induction conditions. The reactivity profiles of the control antibodies is summarized in Tables 4 to 6. The anti-Hsc70 antibody (SPA-815; clone 1B5) is a rat monoclonal antibody originally produced to the CHO (hamster) Hsc70 protein. This antibody was found to react only with Hsc70 protein, no reactivity with any of the inducible isoforms, Grp78, DnaK, or Hsp71 was detected. Anti-Hsp70A (SPA-812) specific antibody is a rabbit polyclonal antibody produced to purified recombinant human Hsp70A protein. This antibody reacted only with the Hsp70A protein, there was no reactivity detected with Hsp70B', Hsp70B fragment, Hsc70, Grp78, E. coli DnaK, and M. tuberculosis Hsp71 proteins in immunoblots. The third control antibody is a mouse monoclonal antibody (SPA-810; clone C92F3A-5) which was originally produced to human Hsc70/Hsp70 proteins purified from HeLa cells. This antibody was found to react with Hsp70A and recombinant Hsp70B', but not with Hsc70, Hsp70B protein fragment, Grp78, DnaK or Hsp71. Other control antibodies included a rabbit Hsp110 polyclonal (SPA-1101), a mouse Grp75 monoclonal (SPA-825; clone 30A5), a mouse monoclonal specific for the ER retention signal peptide KDEL (SPA-827; clone 10C3), a mouse DnaK monoclonal (SPA-880; clone XXX), and a mouse Hsp71 monoclonal (SPA-885; clone 5A8). The Hsp110 and Grp75 antibodies did not react with Hsp70A, Hsp70B', Hsc70, Grp78, DnaK or Hsp71 proteins. The KDEL antibody reacted with Grp78 protein, but not with Hsp70A, Hsp70B', Hsc70, DnaK or Hsp71 proteins. The DnaK and Hsp71 antibodies reacted respectively with DnaK and Hsp71 proteins, but not with Hsp70A, Hsp70B', Hsc70, or Grp78 proteins. Using these control antibodies, Hsp110, Grp75, Hsc70, and KDEL proteins were detected in control and heat stressed human A431 cells, monkey Vero cells, hamster CHO cells and bovine MDBK cells (Table 6). Hsp70A was detected in control A431, Vero and MDBK cells. It was not detected in control CHO cells. Hsp70A was detected at elevated levels in the heat stressed A431, Vero, CHO and MDBK cells.

(Table 5) when assessed by immunoblotting. However, 3/10 CB2 immunized mice either did not detect native Hsp70B' or weakly reacted with other unknown proteins in a lysate. The goat CB2 antisera also specifically detected native Hsp70B' protein, despite low anti-CB2 peptide titres. However, the reactivity of the goat antisera with native Hsp70B' was lower, when compared to the rabbit and mouse CB2 antibodies (Table 5).

TABLE 4

Summary of Anti-HSP70 Antibody Reactivity Profiles with Different HSP70 Family Members

| Epitope (Ab) Name | Location | Hsc70 Reactivity Rec. protein$^\triangledown$ | Hsp70A Reactivity Rec. protein$^\triangledown$ | Hsp70B' Reactivity Rec. protein$^\triangledown$ | Hsp70B Reactivity Rec. protein$^\triangledown$ | Grp78 Reactivity Rec. protein$^\triangledown$ | DnaK Reactivity Rec. protein$^\triangledown$ | Hsp71 Reactivity Rec. protein$^\triangledown$ |
|---|---|---|---|---|---|---|---|---|
| CB | 624–638 | 0 | 0 | 3 | 0 | ♠0 | ND | ND |
| CA | 561–573 | 0 | 0 | 3 | 0 | ND | ND | ND |
| CD | 561–576 | 2 | 1 | 3 | 0 | ND | ND | ND |
| CC | 546–559 | 0 | 0 | 3 | 3 | ND | ND | ND |
| NT | 1–12 | 2 | 2 | 3 | 3 | ND | ND | ND |
| ♦ECB | 618–638 | ♠0 | ♠0 | 3 | ND | ♠0 | ND | ND |
| ♦TCB | 624–635 | ♠0 | ♠0 | 2 | ND | ♠0 | ND | ND |
| ♦CE | 553–567 | 0 | 0 | 3 | ND | 0 | 0 | 0 |
| CB2 (rabbit) | 624–638 | 0 | 0 | 3 | ND | 0 | 0 | 0 |
| ♦CB2 (goat) | 624–638 | ♠0 | ♠0 | 2 | ND | ♠0 | ND | ND |
| ♦CB2 (mouse) | 624–638 | ♠0 | ♠0 | ♠3 | ND | ♠0 | ND | ND |
| *70B' Wp | Hsp70B' 1–643 | 0 | 0 | 2 | ND | 0 | 0 | 0 |
| SPA-810 | 437–504 (Hsp70A) | 0 | 3 | 2 | 0 | 0 | 0 | 0 |
| SPA-812 | Multiple Hsp70A | 0 | 3 | 0 | 0 | 0 | 0 | 0 |
| SPA-815 | Hsc70 | 3 | 0 | 0 | 0 | 0 | 0 | 0 |
| SPA-1101 | Hsp110 626–640 | 0 | 0 | 0 | ND | 0 | 0 | 0 |
| SPA-825 | Grp75 | 0 | 0 | 0 | ND | 0 | 0 | 0 |
| SPA-827 | KDEL | 0 | 0 | 0 | ND | 1 | 0 | 0 |
| SPA-880 | DnaK | 0 | 0 | 0 | ND | 0 | 2 | 0 |
| SPA-885 | Hsp71 | 0 | 0 | 0 | ND | 0 | 0 | 3 |

$^\triangledown$Relative reactivity as assessed by Western blotting analysis of SDS-denatured recombinant proteins. Intensity of the antigen specific bands was scored on a relative scale where 0 = no signal detected and 3 = a very strong signal.
ND = not determined.
♦Representative sera from one animal.
*Pooled sera.
♠Determined with native protein in a cell lysate instead of recombinant protein. Shaded Hsp70B' antibodies are affinity purified.

The nine rabbit anti-peptide antibodies generated to Hsp70B' epitopes reacted with Hsp70B' recombinant protein in Western blot analysis (Table 4). The antibodies also detected Hsp70B' protein only in stressed cell lysates prepared from human cell lines (Tables 5 and 6).

The immunoaffinity purified rabbit anti-CB and CB2 antibody preparations (epitope residues: 624–638) were found to be specific for the Hsp70B' protein; only a single 69 kDa protein is detected on Western blots analysis with complex protein mixtures from total human cell lysates. Although strong reactivity was seen with both native and recombinant Hsp70B', there was no reactivity with recombinant and/or native Hsc70, Hsp70A, DnaK, Hsp71, Hsp110, Grp75, Grp78 and other KDEL proteins (Tables 4–6).

Representative CB2 sera samples from individual mice exhibited specificity to the native Hsp70B' protein in a lysate In any case, CB/CB2 is a unique epitope that can be used reproducibly (i.e. separate occasions, different animals) to generate Hsp70B' specific antibodies. This epitope may be used to generate antibodies, such as monoclonals, of exquisite specificity and useful affinity. The CB/CB2 epitope has already been used to produce mouse hybridomas that react with the CB/CB2 peptides. The reactivity of the hybridomas with Hsp70A and Hsp70B' proteins is currently being evaluated. Ideally, the monoclonal(s) will exhibit the same specificity as the polyclonal CB antibodies and will bind peptide, recombinant and native Hsp70B' with a Ka in the range of $10^4$–$10^{12}$ M$^{-1}$. The antibodies generated to this epitope are excellent candidates for inclusion in the establishment of rapid screening assays.

The peptide immunogens for the ECB and TCB antibodies were based on the CB/CB2 epitopes. The ECB peptide was an extended version of CB/CB2 by six amino acids at the N-terminal end. When ECB sera from three individual rabbits were analyzed by immunoblots, all three rabbits produced antibody that reacted extremely well with purified recombinant Hsp70B' (Table 4) and native Hsp70B' in a lysate (Table 5). However, 1/3 antisera specifically detected Hsp70B' in a lysate. The remaining 2 antisera reacted very weakly with other unknown non-inducible proteins in the cell lysates. This antibody (from 3/3 rabbits), however, did not react with native Hsp70A, Hsc70, Hsp110, Grp75, Grp78 or other KDEL proteins. Any weak binding to the unknown lysate proteins can likely be "diluted out" or the antibody could be affinity purified to improve specificity. If successful, the ECB antibody could be used in conjunction with other Hsp70B' antibodies, such as CE, CA, or CC, for immunoassay development. The ECB epitope would also be a good candidate for a monoclonal antibody development.

Anti-TCB was generated with a CB/CB2 peptide that was truncated by three amino acids at the C-terminal. Although the TCB antisera from 3/3 rabbits reacted well to the immunizing peptide (Table 1), only 1/3 rabbits produced antibody that reacted with recombinant (Table 4) and native Hsp70B' (Table 5), and an unknown non-inducible 40 kDa protein in immunoblots. The reactivity with the non-inducible protein can likely be "diluted out" or the antibody can be purified to improve specificity. The sera from the two other TCB immunized rabbits reacted with just recombinant Hsp70B' and not the native form (Table 5), suggesting differences in protein folding and surface exposure between the recombinant and native proteins. These two antisera also reacted with other unknown non-inducible proteins. The antisera from all three rabbits did not react with Hsp70A or Hsc70. The lower success ratio (i.e. 1/3 rabbits detected native Hsp70B') with the TCB peptide suggests an importance for the three omitted GPI amino acids present on the CB/CB2 and ECB epitopes. Based on relative titre index, the CB2, 70B' WP and ECB antibodies exhibited no to low reactivity with the TCB peptide (Table 2), but these three antibodies reacted with both recombinant and native Hsp70B'. This supports the importance of the GPI residues for Hsp70B' antibody production, despite predictions of low antigenicity and surface probability. Taken together, TCB polyclonals that recognize native Hsp70B' may be problematic to produce and resupply for industrial immunoassay uses.

The anti-"CA" antibody (epitope residues: 561–573) recognizes the Hsp70B' protein but not the Hsc70, Hsp70A nor the Hsp70B (fragment) purified proteins. This antibody does, however, identify other unknown proteins of lower and higher molecular weight. As long as the interpretation of binding reactivity of this antibody on immunoblots is restricted to a window of 60–80 kDa, this antibody will act as a sensitive and specific probe in immunoblot analysis for the Hsp70B' protein. None of the other proteins seen on immunoblots with this antibody are stress inducible under the conditions of these experiments. The non-Hsp70B' proteins are detected equally well in both stressed and unstressed cell lysates. Although this antibody can be used in immunoblot analysis for the specific detection of the Hsp70B' protein the cross-reactivity of this antibody for other cellular proteins decreases the usefulness of the antibody in immunoassay rapid screening tests. However, in combination with another specific antibody such as "CB", this antibody may be a useful component in immunossays.

The anti-"CD" antibody (epitope residues: 561–576) recognizes both recombinant and native Hsp70B' as well as the constitutive Hsc70 protein. The inducible Hsp70A protein is also weakly recognized by this antibody. In addition, this antibody will detect, on immunoblot analysis, some unknown lower molecular weight constitutively expressed proteins. The large variation in "CA" and "CD" antibody is surprising as the peptides used to generate these antibodies were very similar. The "CD" peptide is identical to the "CA" peptide with three exceptions; (a) the "CD" peptide lacks the additional N-terminal cysteine residue used to facilitate coupling of the "CA" peptide to KLH, (b) the coupling to KLH was modified to coupling through the natural cysteine sequence at the carboxy-terminus, and (c) three additional (DKC) residues were added to the carboxyl-terminus of the "CD" epitope. These three additional residues are conserved in Hsc70, Hsp70A as well as in Hsp70B' sequences and are predicted to lie within a hydrophobic region which is predicted in the Emini analyses to be antigenic. As the molecular weights of the 3 proteins are different; 69, 72 and 73 for the Hsp70B', Hsp70A and Hsc70 proteins respectively, expression patterns of the different Hsp's may be differentiated with this antibody on immunoblot analysis. However, due to the cross-reactivity of this antibody for other Hsp family members as well as other cellular proteins this antibody would not be useful in rapid screening immunoassays.

The anti-"CC" antibody (epitope residues: 546–559) recognizes both Hsp70B (fragment) and Hsp70B' recombinant proteins. This antibody does not recognize either the Hsc70 cognate protein nor the stress inducible Hsp70A protein. Although some additional unknown higher and lower molecular weight proteins are detected on immunoblots with this antibody, these proteins are also not inducible under these conditions and do not fall within the 60–80 kDa window for evaluation. This antibody is, therefore, useful for immunoblot analysis but due to cross-reactivity with other cellular proteins the utility of this antibody in immunoassay analysis is decreased. However, in combination with another specific antibody such as "CB", this antibody may be a useful component in immunossays.

The CE antibody was made from a peptide which combined seven amino acids from the C-terminal of CC and seven amino acids from the N-terminal of CA, linked via a leucine residue. Specific Hsp70B' binding was observed with CE antisera from 1/3 rabbits in immunoblots (Table 5). There was no reactivity with Hsp70A, Hsc70, Hsp110, Grp75, DnaK, Hsp71, Grp78 or other KDEL proteins. The CA and CC antibodies both detected non-inducible proteins in addition to Hsp70B'; the CE antisera from this particular rabbit did not. Like the CB2 antibody, the CE antisera from this rabbit only detected human Hsp70B' in lysates. There was no reactivity with any proteins in monkey, hamster or bovine cell lysates. CE antisera from another rabbit reacted with recombinant and to a lesser degree with native Hsp70B' (Table 5), but also weakly with other non-inducible proteins. Interestingly, the more specific CE antisera had an eight fold lower anti-CE peptide titre than the non specific CE antisera (Table 1). The CE antisera from the remaining rabbit reacted with several non-inducible proteins in a lysate and very minimally with recombinant Hsp70B'. Reactivity of this antisera with native protein was inconclusive since many proteins were detected in the expected 70 kDa molecular weight range. Although the CE antibody has a lower success ratio, a monoclonal antibody may be beneficial if it exhibits the same reactivity as the specific polyclonal. Because the locations of the CE and CB/CB2 or ECB peptides are distinct, specific monoclonal antibodies to these epitopes would be choice components for two-site immunoassay development.

The "NT" antibody (epitope residues: 1–12) is an area of sequence of relative sequence homology within the Hsp70 family. This epitope has an overall homology of less than 50% with other HSP70 family members, however, the areas of sequence identity are sequential. The anti-"NT" antibody is useful as an HSP70 family marker, but has no utility in the differential detection of different Hsp70 family members.

The 70B' WP antibody specifically detected both recombinant and native Hsp70B' in immunoblots. When the antibody was used at higher dilutions (i.e., 1:20000), no cross reactivity with other HSP70 homologs or other lysate proteins was observed. This antibody may be a useful component in immunoassays if used at higher dilutions, purified or in conjunction with another specific antibody such as CB/CB2, ECB or CE. This antibody had relatively low titre index values with the CB, ECB, TCB and CE peptides), but a high value with Hsp70B' (Table 2). This suggests that other specific epitopes, perhaps conformational, exist for Hsp70B' monoclonal antibody production that require whole protein immunizations to exploit.

Summary of Hsp70B'Antibody Specificity. Table 7 summarizes the assessment of specificity for the rabbit Hsp70B' antibodies with respect to the three methods performed: relative titre index, competition EIA and immunoblotting. Only one antibody, CB2 was considered specific for Hsp70B' in all three methods of assessment. Since CB was generated with the same peptide sequence, it is likely that this antibody would also be considered Hsp70B' specific for all three assessments methods. The ECB, CE and 70B' WP antibodies could likely be purified or used at higher dilutions to maximize specificity. The CD and NT antibodies were not useful for distinguishing Hsp70B' from other HSP70 homologs, illustrating that the peptide approach is not 100% successful for generating Hsp70B' antibodies.

TABLE 5

Reactivity of Hsp70B', Hsp70A and Hsc70 Antibodies with 68kDa (Hsp70B') Protein from Unstressed and Heat Stressed Human Cell Lysates

| Antibody Designation | Antigen Epitope | Animal Number | HeLa | HeLa HS | Jurkat | Jurkat HS | A431 | A431 HS |
|---|---|---|---|---|---|---|---|---|
| CB | 624–638 | N/A | 0 | +3 | 0 | +3 | 0 | +3 |
| CA | 561–573 | N/A | 0 | +3 | 0 | +3 | 0 | +3 |
| CD | 561–576 | N/A | 0 | +3 | 0 | +3 | 0 | Not tested |
| CC | 546–559 | N/A | 0 | +3 | 0 | +3 | 0 | +3 |
| NT | 1–12 | N/A | +3 | +3 | +3 | +3 | Not tested | Not tested |
| ◆ECB | 618–638 | 1 | 0 | 3 | Not tested | Not tested | Not tested | Not tested |
|  |  | 2 | 0 | 3 | Not tested | Not tested | Not tested | Not tested |
|  |  | 3 | 0 | 3 | Not tested | Not tested | Not tested | Not tested |
| ◆TCB | 624–635 | 1 | 0 | 2 | Not tested | Not tested | Not tested | Not tested |
|  |  | 2 | 0 | 0 | Not tested | Not tested | Not tested | Not tested |
|  |  | 3 | 0 | 0 | Not tested | Not tested | Not tested | Not tested |
| ◆CE | 553–567 | 1 | 0 | 3 | Not tested | Not tested | 0 | 3 |
|  |  | 2 | 0 | 1 | Not tested | Not tested | Not tested | Not tested |
|  |  | 3 | Not tested | Not tested | Not tested | Not tested | 2 | 2 |
| CB2 (rabbit) | 624–638 | N/A | Not tested | Not tested | 0 | 3 | 0 | 3 |
| ◆CB2 (goat) | 624–638 | 1 | 0 | 1 | Not tested | Not tested | Not tested | Not tested |
| ♣CB2 (mouse) | 624–638 | 1 | 0 | 3 | Not tested | Not tested | Not tested | Not tested |
|  |  | 2 | 0 | 3 | Not tested | Not tested | Not tested | Not tested |
|  |  | 3 | 0 | 2 | Not tested | Not tested | Not tested | Not tested |
|  |  | 4 | 0 | 1 | Not tested | Not tested | Not tested | Not tested |
|  |  | 5 | 0 | 0 | Not tested | Not tested | Not tested | Not tested |
| *70B' WP | Hsp70B 1–643 | N/A | Not tested | Not tested | Not tested | Not tested | 0 | 2 |
| SPA-810 | Hsp70A 437–504 | N/A | +2 | +3 | +2 | +3 | +2 | +3 |
| SPA-812 | Hsp70A Multiple | N/A | +3 | +3 | +1 | +2 | +2 | +2 |
| SPA-815 | Hsc70 Unknown | N/A | +3 | +3 | +2 | +3 | +3 | +3 |

In Table 5, reactivity levels were assessed by immunoblotting analysis of 10–20 μg lysate. Intensity of antigen specific was scored on a relative scale where 0 = no signal and 3 = a very strong signal.
☐Relative reactivity levels are reported for unpooled serum antibodies from individual animals.
☐Relative reactivity levels are reported for 5/10 mice.
* Relative reactivity levels are reported for pooled serum antibodies. Shaded areas represent inconclusive binding to Hsp70B'.
N/A in the Animal Number column indicates purified antibody.

TABLE 6

Reactivity of Hsp Antibodies with Control and Heat Stressed Mammalian Cell Lysates

| Antibody | Location | A431 | A431 HS | Vero | Vero HS | CHO | CHO HS | MDBK | MDBK HS |
|---|---|---|---|---|---|---|---|---|---|
| CB2 | Hsp70B' 624–638 | 0 | +3 | 0 | 0 | 0 | 0 | 0 | 0 |
| CE | Hsp70B' 553–567 | 0 | +3 | 0 | 0 | 0 | 0 | 0 | 0 |
| 70B' WP | Hsp70B' 1–643 | 0 | +2 | 0 | 0 | 0 | 0 | 0 | 0 |

TABLE 6-continued

Reactivity of Hsp Antibodies with Control and Heat Stressed Mammalian Cell Lysates

| Antibody | Location | A431 | A431 HS | Vero | Vero HS | CHO | CHO HS | MDBK | MDBK HS |
|---|---|---|---|---|---|---|---|---|---|
| SPA-1101 | Hsp110 626–640 | +2 | +2 | +2 | +1 | +2 | +2 | +2 | +2 |
| SPA-810 | Hsp70A 437–504 | +2 | +3 | +2 | +3 | 0 | +2 | +1 | +3 |
| SPA-812 | Hsp70A Multiple | +2 | +3 | +2 | +3 | 0 | +1 | +1 | +2 |
| SPA-815 | Hsc70 Unknown | +3 | +3 | +3 | +3 | +3 | +3 | +3 | +3 |
| SPA-825 | Grp75 Unknown | +3 | +3 | +3 | +3 | +3 | +3 | +3 | +3 |
| SPA-827 | KDEL 649–654 | +1 | +2 | +2 | +2 | +3 | +3 | +1 | +1 |
| SPA-880 | DnaK Unknown | 0 | 0 | 0 | 0 | 0 | 0 | 0 | 0 |
| SPA-885 | Hsp71 Unknown | 0 | 0 | 0 | 0 | 0 | 0 | 0 | 0 |

Reactivity levels were assessed by immunoblotting analysis of 10–20 mg lysate. Intensity of antigen specific bands was scored on a relative scale where 0 = no signal and 3 = a very strong signal.
  Relative reactivity levels are reported for unpooled serum antibodies from individual animals.
§Relative reactivity levels are reported for 5/10 mice.
*Relatvie reactivity levels are reported for pooled serum antibodies.
Shaded areas represent inconclusive binding to Hsp70B'.
N/A in the Animal Number column indicates purified antibody.

TABLE 7

Summary of Rabbit Hsp70B' Antibody Specificity

| Antibody | Location | Method for Specificity Assessment | | |
|---|---|---|---|---|
| Name | Hsp70B' | Relative Titre Index | Competition EIA | Immunoblot |
| CB | 624–638 | ND | ND | specific for recombinant and native Hsp70B' |
| CA | 561–573 | ND | ND | detects other proteins in cell lysates; i.e. not specific |
| CD | 561–576 | ND | ND | Cross reactivity with other HSP70 family members and cellular proteins; i.e. not specific |
| CC | 546–559 | ND | ND | detects other proteins in cell lysates; i.e. not specific |
| NT | 1–12 | ND | ND | detects other HSP70 family members; i.e. not specific |
| ECB | 618–638 | Specific for Hsp70B' | ND | One bleed specific for Hsp70B'; other bleeds weakly detect other proteins, but can likely be diluted out |
| TCB | 624–635 | Specific for Hsp70B' | ND | Not specific; 2/3 bleeds did not detect native Hsp70B' |
| CE | 553–567 | Specific for Hsp70B' | Specific for Hsp70B' | One bleed specific for Hsp70B'; 2/3 bleeds not specific |
| CB2 | 624–638 | Specific for Hsp70B' | Specific for Hsp70B' | Specific for Hsp70B' |
| 70B' WP | 1–643 | Not specific for Hsp70B' at lower dilutions | Specific for Hsp70B' when used at a high dilution | Specific for Hsp70B' when used at a high dilution |

Relative reactivity levels were assessed by Western blotting analysis of 10 µg of total cell lysate. Immounoblots were probed with the Hsp70B' antibodies, CB2, CE and 70B' WP, as well as anti-HSP antibodies specific for Hsp110, Hsp70A, Hsc70, Grp75, KDEL, DnaK and Hsp71. The CE antibody used for this study was the sera specific for Hsp70B' from one rabbit. Immunoblots were developed by ECL. Intensity of the antigen specific bands was scored on a relative scale where 0 = no signal detected and 3 = a very strong signal.

Hsp70B' Protein: Distribution and Induction Conditions. As can be seen in Tables 5, 6 and 8, the Hsp70B' antibodies (NT, CA, CB, CC, CD, ECB, TCB, CB2, CE and 70B' WP) detect the Hsp70B' protein only in stressed human tissues, no reactivity is detected in non-stressed cells or tissues.

TABLE 8

Reactivity of Anti-Hsp70B' "CB" Antibody with a Panel of Different Cell Lysates from a Variety of Different Tissue Sources and Different Species

| Cell Line Designation | Description | Species | Reactivity (non-stressed) | Reactivity (stressed) |
|---|---|---|---|---|
| HeLa | Epitheloid carcinoma, cervix | Human | Negative | +3 |
| A431 | Epidermoid carcinoma | Human | Negative | +3 |
| Jurkat | Adult T-cell leukemia | Human | Negative | +2 |
| H4 | Neuroglioma, brain | Human | Negative | +1 |
| MCF7 | Breast adenocarcinoma, pleural effusion | Human | Negative | +(weak) |

TABLE 8-continued

Reactivity of Anti-Hsp70B' "CB" Antibody with a Panel of Different Cell Lysates from a Variety of Different Tissue Sources and Different Species

| Cell Line Designation | Description | Species | Reactivity (non-stressed) | Reactivity (stressed) |
|---|---|---|---|---|
| HMEC | Mammary epithelial cells (normal) | Human | Negative | Not tested |
| HRCE | Renal cortical epithelial cells (normal) | Human | Negative | Not tested |
| RPTEC | Renal proximal tubule epithelial cells (normal) | Human | Negative | Not tested |
| NHBE | Bronchial epithelial cells (normal) | Human | Negative | Not tested |
| PrEC | Prostate epithelial cells (normal) | Human | Negative | Not tested |
| NHEK-Ad | Epidermal keratinocytes adult (normal) | Human | Negative | Not tested |
| NHEK-Neo | Epidermal keratinocytes neo (normal) | Human | Negative | Not tested |
| NHEF-Neo pool | Epidermal keratinocytes neo pool (normal) | Human | Negative | Not tested |
| NHDF-Ad | Dermal fibroblast adult (normal) | Human | Negative | Not tested |
| NHDF-Neo | Dermal fibroblast neo (normal) | Human | Negative | Not tested |
| HMVEC-d Ad | Microvascular endothelial adult (normal) | Human | Negative | Not tested |
| HMVEC-d Neo | Microvascular endothelial neo (normal) | Human | Negative | Not tested |
| NHEM | Melanocytes Neo (normal) | Human | Negative | Not tested |
| HPAEC | Pulmonary artery endothelial cells (normal) | Human | Negative | Not tested |
| HCAEC | Coronary artery endothelial cells (normal) | Human | Negative | Not tested |
| HIAEC | Lliac artery endothelial cells (normal) | Human | Negative | Not tested |
| HAEC | Aortic endothelial cells (normal) | Human | Negative | Not tested |
| HMVEC-L | Lung microvascular endothelial cells (normal) | Human | Negative | Not tested |
| HUVEC | Umbilical vein endothelial cells (normal) | Human | Negative | Not tested |
| HUAEC | Umbilical artery endothelial cells (normal) | Human | Negative | Not tested |
| AoSMC | Aortic artery smooth muscle cells (normal) | Human | Negative | Not tested |
| BSMC | Bronchial/trachial smooth muscle cells (normal) | Human | Negative | Not tested |
| CASMC | Coronary artery smooth muscle cells (normal) | Human | Negative | Not tested |
| PASMC | Pulmonary artery smooth muscle cells (normal) | Human | Negative | Not tested |
| UASMC | Umbilical artery smooth muscle cell (normal) | Human | Negative | Not tested |
| UtSMC | Uterine smooth muscle cells (normal) | Human | Negative | Not tested |
| SkMC | Skeletal muscle cells (normal) | Human | Negative | Not tested |
|  | Liver (normal tissue) | Human | Negative | Not tested |
|  | Lung (normal tissue) | Human | Negative | Not tested |
|  | Brain (normal tissue) | Human | Negative | Not tested |
|  | Kidney (normal tissue) | Human | Negative | Not tested |
|  | Testis (normal tissue) | Human | Negative | Not tested |
|  | Ovary (normal tissue) | Human | Negative | Not tested |
|  | Heart (normal tissue) | Human | Negative | Not tested |
|  | Spleen (normal tissue) | Human | Negative | Not tested |
| VERO | Kidney | Monkey | Negative | Negative |
| L929 | Connective tissue | Mouse | Negative | Negative |
| 3T3 | Embryo | Mouse | Negative | Negative |
| Rat2 | Embryo | Rat | Negative | Negative |
| GPC-16 | Colon, adenocarcinoma | Guinea pig | Negative | Negative |
| MDOK | Kidney | Sheep | Negative | Negative |
| MDBK | Kidney | Cow | Negative | Negative |
| ESK4 | Kidney | Pig | Negative | Negative |

As can be seen in Tables 3 and 4 the Hsp70B' antibodies (NT, CA, CB, CC and CD) detect the Hsp70B' protein only in stressed human tissues, no reactivity is detected in non-stressed cells or tissues. Eight different normal human tissues, 27 samples of cell line lysates derived from normal human sources, five samples of cell line lysates derived from neoplastic tissues and seven other mammalian species were evaluated for the expression of the Hsp70B' protein. The Hsp70B' protein was not detected by the anti-Hsp70B' antibody "CB" in the 48 samples obtained from "normal" or "unstressed" cells. If these cells are exposed to elevated temperatures, the Hsp70B' protein is expressed in all of the heat-shocked human cell lines evaluated. These results are consistent with earlier findings at the mRNA level, using specific oligonucleotide probes (Leung et al., Biochem. J. 267:125–132, 1990; Leung et al., Genomics 12:74–79, 1992). These investigations did not detect the presence of any hsp70B' mRNA in the unstressed cells.

The temperature threshold of Hsp70B' protein expression in heat treated HeLa cells following recovery for 0, 2.5, 5, 16 and 24 hours at 37° C. was investigated. In this study the level of expression of the Hsp70B' protein was greatest at the 16 hour (+2) timepoint. Therefore if a significant level of Hsp70B' protein was detected, this would imply that the cells or individual tested was either currently or had recently been exposed to a significant stressor and not due to a stressful situation occurring far in the past. The stress response does, however, persist long enough to be potentially useful as a diagnostic probe. The persistence of the Hsp70B' protein in cells following stress is similar to the results described for Hsp70A protein in recovering peripheral blood lymphocytes (Bratton et al., *Int. J. Hyperthermia* 13(2):157–168, 1997). These investigators found that the Hsp70A protein persisted for at least 48 hours and reached maximal expression at 12 hours.

constitutive Hsc70 protein is not affected by exposure to the proline analogue azetidine, to the heavy metals $CdCl_2$ or $ZnCl_2$ or to increased temperature. The inducible Hsp70A stress protein appears to be expressed at high levels basal levels in unstressed cells as has been found previously by other investigators (Turman et al., *Biochemical and Molecular Medicine* 60:49–58, 1997). Changes to the level of Hsp70A protein expression was found to be obscured in these investigations by the high basal level of expression of this protein. The induction as a result of stress treatment is consistent with published findings. The extent to which Hsp70A expression is induced by heat shock is inversely correlated with initial levels of Hsp70A (Turman et al., *Biochemical and Molecular Medicine* 60:49–58, 1997). Therefore, in human cells, high basal expression of Hsp70A may prevent further induction of HSP70 after heat shock.

TABLE 9

Investigation of the Induction$^\nabla$ of Hsc70, Hsp70A and Hsp7B' Proteins*
in Human Cell Lines Under Different Induction Conditions

| Cell Line | HeLa Cells | | | | Jurkat Cells | | | | A431 Cells | | | |
| --- | --- | --- | --- | --- | --- | --- | --- | --- | --- | --- | --- | --- |
| Antigen | Hsc70 | Hsp70A/B' | Hsp70A | Hsp70B' | Hsc70 | Hsp70A/B' | Hsp70A | Hsp70B' | Hsc70 | Hsp70A/B' | Hsp70A | Hsp70B' |
| Non-stressed | +3 | +2 | +2 | 0 | +3 | +1 | +1 | 0 | +3 | +2 | +2 | 0 |
| Heat (430 C.) 20 min. | +3 | +2 | +2 | +1 | +3 | +2 | +2 | +3 | +3 | +3 | +2 | +3 |
| Heat (430 C.) 120 min. | +3 | +3 | +3 | +3 | +3 | +2 | +2 | +3 | +3 | +3 | +2 | +3 |
| Azetidine (5 μM, 5 hours) | +3 | +3 | +3 | +1 | +3 | +2 | +2 | +1 | +3 | +3 | +2 | +2 |
| CdCl2 (100 μM, 2 hours) | +3 | +3 | +3 | +2 | +3 | +2 | +2 | +3 | +3 | +3 | +2 | +1 |
| ZnCl2 (250 μM, 2 hours) | +3 | +3 | +3 | +1 | +3 | +1 | +2 | +1 | +3 | +3 | +2 | +2 |

$^\nabla$Relative protein levels as assessed by Western blotting analysis of 20 ug of total cell lysate. Intensity of the antigen specific bands was scored on a relative scale where 0 = no signal detected and 3 = a very strong signal
*Immunoblots were carried out using the following antibodies: SPA-815 (Hsc70), SPA-810 (Hsp70A and Hsp70B'), SPA-812 (Hsp70A, Hsp70B') and CB (Hsp70B'). Polyclonal antibodies to the CA and CC Hsp70B' epitopes were also checked for reactivity with these cell lines under these conditions. The relative levels of the Hsp70B' proteins measured with these antibodies agree in all cases with the profiles seen in immunoblots with the anti-CB antibody.

TABLE 10

Dose Response Curve Showing the Relative Induction [□ of Human Hsp70 Family
Members in HeLa Cells Heat Stressed at Different Temperatures.

| Heatshock temperature (° C.) | Hsc70 SPA-815 | Hsp70A/ Hsp70B' SPA-810 | Hsp70A SPA-812 | Hsp70B'/ Hsp70B CB | Hsp70B'/ Hsp70B CA | Hsp70B'/ Hsp70B CC |
| --- | --- | --- | --- | --- | --- | --- |
| 37 | 3 | 3 | 2 | 0 | 0 | 0 |
| 38.5 | 3 | 3 | 2 | 0 | 0 | 0 |
| 40 | 3 | 3 | 2 | 0 | 0 | 0 |
| 41.5 | 3 | 3 | 2 | 2 | 1 | 2 |
| 43 | 3 | 3 | 2 | 3 | 3 | 3 |
| 44.5 | 3 | 3 | 2 | 3 | 3 | 3 |

*Relative protein levels as assessed by Western blotting analysis of 20 ug of total cell lysate. Intensity of the antigen specific bands was scored on a relative scale where 0 = no signal detected and 3 = a very strong signal)

The relative induction of the Hsc70, Hsp70A and Hsp70B' proteins under different conditions were evaluated in HeLa, Jurkat and A-431 human cell lines (Tables 9 and 10). It can be seen that the induction of the Hsp70B' protein was different than that seen for other HSP70 isoforms. Hsp70B' protein was not present in unstressed cells and was induced only in response to cellular stress. The expression of the The Hsp70B' protein was not present in unstressed cells. Slight temperature increases up to 40° C. did not elicit a response. Once the threshold of 41.5° C. was reached, all three human cell lines (Hela, Jurkat and A-431) responded by expressing the Hsp70B' protein. This induction threshold of Hsp70B' expression is different than the threshold described previously in which hsp70B' mRNA levels were measured using specific oligonucleotides (Leung et al., *Biochem. J.* 267:125–132, 1990). These investigators reported that hsp70B' mRNA was strongly induced at 45° C. and was not detectable after 42° C. treatment. Furthermore, they found only trace amounts of hsp70B' mRNA after $CdCl_2$ treatment in contrast to the protein data reported here (Table 5). The Hsp70B' protein was shown to be induced by the proline analog azetidine as well as the heavy metals $CdCl_2$ and $ZnCl_2$, all known inducers of stress proteins. This discrepancy in the induction threshold as determined at the genomic and protein levels is likely due to the inherent technical differences in the two techniques. Previous studies looking at regulation of the hsp70A and hsc70 genes have not yielded a consistent set of results (Hansen et al., *Exp. Cell Research* 192:587–596, 1991; Mangurten et al., *Cell Stress & Chaperones* 2(3):168–174, 1997). Depending on the particular system and at what level expression was examined, hsc70 expression can either increase or decrease following treatment with agents to induce differentiation. In studies of the differential expression of Hsp70A in wound healing, it was found that whilst hsp70A mRNA did not show significant correlation with healing, a strong correlation was seen between well healing wounds and expression of the Hsp70A protein (Oberringer et al., *Biochemical and Biophysical Research Communications* 214(3):1009–1014, 1995). It would be preferable to measure the protein, since the protein response persists whereas the mRNA has been reported to have a very short half-life (Bratton et al., *Int. J. Hyperthermia* 13(2):157–168, 1997).

At the level of transcription the hsp70A gene is regulated through transcription factors other than HSF's under non-stressed conditions and therefore, the Hsp70A protein is detected even in the physiological state (Hansen et al., *Exp. Cell Research* 192:587–596, 1991). The hsp70B' gene is regulated exclusively by the association of HSF's and the heat shock element, allowing no constitutive expression (Suzuki et al., *Radiation Research* 149: 195–201, 1998). The promoter regions of hsp70B' and hsp70B genes differ extensively from the hsp70A gene in that they lack TATA and CAAT boxes which are believed to contribute to the basal expression of Hsp70A (Wu et al., *Proc. Natl. Acad. Sci., USA* 83(3):629–633, 1986; Greene et al., *Mol. Cell Biol.* 7(10):3646–55, 1987). The two hsp70B DNA homologs display differences in their 5' regions as well as several changes within key promoter sequences. The hsp70B' gene has been shown to have a 19-nucleotide-residue insertion in the hsp70B gene that lies within the heat-shock element of the hsp70B DNA sequence (Leung et al., *Genomics* 12:74–79, 1992). Elevated mRNA levels do not always translate into increased protein levels due to regulation at the transcriptional and/or post-transcriptional levels (Oberringer et al., *Biochemical and Biophysical Research Communications* 214(3):1009–1014, 1995). Using the anti-Hsp70B' antibodies in immunochemical testing procedures, therefore, allows a more sensitive, longer lasting quantitative evaluation of Hsp70B' protein levels than that found using specific oligonucleotides to evaluate mRNA levels.

The Hsp70B' protein has been shown to be expressed only following significant stress on the cell or organism, whether this stress is caused by elevated heat or exposure to heavy metals or toxic chemicals. The Hsp70B' antibodies of the present invention offer a unique opportunity to use these naturally occurring biomarkers to evaluate the stress on a system. The nature of the stress need not be known. Monitoring the Hsp70B' biomarker provides a prognostic indicator of the general "wellness" of the cell or organism and indicate when a significant perturbation has occurred. As biomarkers, Hsp's provides sensitive early-warning of toxicity, perhaps allowing intervention at an earlier more tractable stage of the problem.

All publications and patent applications mentioned in this specification are herein incorporated by reference to the same extent as if each individual publication or patent application was specifically and individually incorporated by reference. From the foregoing, it will be evident that, although specific embodiments of the invention have been described herein for purposes of illustration, various modifications may be made without deviating from the spirit and scope of the invention.

What claimed is:

1. An isolated antibody that specifically binds a peptide consisting of the amino acid sequence CGTQARQGDPST-GPI (SEQ ID NO:2).

2. The antibody of claim 1, wherein the antibody is a monoclonal antibody.

3. A kit comprising the antibody of claim 1.

4. The kit of claim 3, further comprising the an Hsp70B' protein or an Hsp70B' peptide.

5. A method of obtaining the antibody of claim 1, the method comprising administering to an animal a peptide consisting of the amino acid sequence CGTQARQGDPST-GPI (SEQ ID NO:2).

6. A method of obtaining the antibody of claim 1, the method comprising administering to an animal a peptide consisting of the amino acid sequence CGTQARQGDPST-GPI (SEQ ID NO:2) and a carrier that enhances the immunogenicity of the peptide and, optionally, a linker between the peptide and the carrier.

7. The method of claim 5, wherein the antibody is a monoclonal antibody.

8. A method of determining whether a cell has been exposed to a stressful environment or a stressful substance, the method comprising performing an immunoassay in which proteins in or on the cell or proteins extracted from the cell are exposed to the antibody of claim 1, wherein binding between a protein in or on the cell or a protein extracted from the cell and the antibody indicates that the cell has been exposed to a stressful environment or a stressful substance.

9. The kit of claim 3, wherein the antibody is a monoclonal antibody.

10. The kit of claim 3, further comprising instructions for use.

11. The kit of claim 4, further comprising instructions for use.

12. The kit of claim 4, wherein the antibody is a monoclonal antibody.

13. The kit of claim 10, wherein the antibody is a monoclonal antibody.

14. The kit of claim 11, wherein the antibody is a monoclonal antibody.

15. The method of claim 6, wherein the carrier is keyhole limpet hemocyanin.

16. The method of claim 6, wherein the antibody is a monoclonal antibody.

17. The method of claim 15, wherein the antibody is a monoclonal antibody.

18. The method of claim 8, wherein the antibody is a monoclonal antibody.

19. The method of claim 8, wherein the antibody has a relative titre index greater than one.

20. The method of claim 5, further comprising collecting blood from the animal.

21. The method of claim 20, further comprising purifying the antibody by immunoaffinity.

* * * * *